(12) United States Patent
Liu et al.

(10) Patent No.: US 8,691,729 B2
(45) Date of Patent: Apr. 8, 2014

(54) REACTION DISCOVERY SYSTEM

(75) Inventors: David R. Liu, Lexington, MA (US); Matthew William Kanan, Palo Alto, CA (US); Mary M. Rozenman, New York, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 1428 days.

(21) Appl. No.: 11/971,642

(22) Filed: Jan. 9, 2008

(65) Prior Publication Data

US 2011/0312507 A1 Dec. 22, 2011

Related U.S. Application Data

(63) Continuation of application No. PCT/US2006/027354, filed on Jul. 14, 2006.

(60) Provisional application No. 60/699,735, filed on Jul. 15, 2005.

(51) Int. Cl.
*C40B 30/08* (2006.01)

(52) U.S. Cl.
USPC .......................................................... 506/11

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,835,312 A | 5/1989 | Itoh et al. | |
| 4,863,857 A | 9/1989 | Blalock et al. | |
| 5,162,218 A | 11/1992 | Schultz | |
| 5,270,170 A | 12/1993 | Schatz et al. | |
| 5,457,111 A | 10/1995 | Luly et al. | |
| 5,539,082 A | 7/1996 | Nielsen et al. | |
| 5,573,905 A | 11/1996 | Lerner et al. | |
| 5,574,141 A | 11/1996 | Seliger et al. | |
| 5,597,697 A | 1/1997 | Diamond | |
| 5,639,603 A | 6/1997 | Dower et al. | |
| 5,677,467 A | 10/1997 | Hoye et al. | |
| 5,698,685 A | 12/1997 | Summerton et al. | |
| 5,708,153 A | 1/1998 | Dower et al. | |
| 5,719,262 A | 2/1998 | Buchardt et al. | |
| 5,721,099 A | 2/1998 | Still et al. | |

(Continued)

FOREIGN PATENT DOCUMENTS

| | | |
|---|---|---|
| EP | 0604552 | 8/1993 |
| EP | 0643778 | 3/1995 |

(Continued)

OTHER PUBLICATIONS

Acevedo, et al., "Non-Enzymatic Transcription of an Oligodeoxynucleotide 14 Residues Long" *J. Mol. Biol.* 197: 187-193, 1987.

(Continued)

*Primary Examiner* — Christian Boesen
(74) *Attorney, Agent, or Firm* — Wolf, Greenfield & Sacks, P.C.; C. Hunter Baker

(57) ABSTRACT

A novel reaction discovery system that does not depend on DNA duplex formation is provided. The advantages of this system include exploring reactions conditions not possible where DNA hybridization is required. For example, the inventive reaction discovery system allows for reaction conditions using organic solvents, higher temperatures, and water-insoluble reagents, catalysts, and ligands. The invention also provides single-stranded oligonucleotide templates with substrate pairs covalently attached and methods of screening for reaction conditions that result in a direct covalent bond between the substrates. Kits are also provided for practicing this novel reaction discovery system.

3 Claims, 22 Drawing Sheets

Selection for Bond-Formation from a Single-Pool Reaction Discovery System

(56) References Cited

U.S. PATENT DOCUMENTS

| | | | |
|---|---|---|---|
| 5,723,598 | A | 3/1998 | Lerner et al. |
| 5,770,358 | A | 6/1998 | Dower et al. |
| 5,786,461 | A | 7/1998 | Buchardt et al. |
| 5,789,162 | A | 8/1998 | Dower et al. |
| 5,811,238 | A | 9/1998 | Stemmer et al. |
| 5,840,485 | A | 11/1998 | Lebl et al. |
| 5,843,701 | A | 12/1998 | Gold et al. |
| 5,846,839 | A | 12/1998 | Gallop et al. |
| 5,880,280 | A | 3/1999 | Organ et al. |
| 5,922,545 | A | 7/1999 | Mattheakis et al. |
| 5,958,691 | A | 9/1999 | Pieken et al. |
| 5,958,703 | A | 9/1999 | Dower et al. |
| 5,986,053 | A | 11/1999 | Ecker et al. |
| 5,998,140 | A | 12/1999 | Dervan et al. |
| 6,037,120 | A | 3/2000 | Benner |
| 6,060,596 | A | 5/2000 | Lerner et al. |
| 6,080,826 | A | 6/2000 | Grubbs et al. |
| 6,127,154 | A | 10/2000 | Mosbach et al. |
| 6,140,493 | A | 10/2000 | Dower et al. |
| 6,140,496 | A | 10/2000 | Benner |
| 6,143,497 | A | 11/2000 | Dower et al. |
| 6,165,717 | A | 12/2000 | Dower et al. |
| 6,175,001 | B1 | 1/2001 | Barbas et al. |
| 6,194,550 | B1 | 2/2001 | Gold et al. |
| 6,207,446 | B1 | 3/2001 | Szostak et al. |
| 6,214,553 | B1 | 4/2001 | Szostak et al. |
| 6,368,808 | B2 | 4/2002 | Sato et al. |
| 6,387,901 | B1 | 5/2002 | Chupak |
| 6,700,025 | B2 | 3/2004 | Moriarty et al. |
| 6,774,229 | B2 | 8/2004 | Mueller et al. |
| 7,070,928 | B2 | 7/2006 | Liu et al. |
| 7,223,545 | B2 | 5/2007 | Liu et al. |
| 2003/0113738 | A1 | 6/2003 | Liu et al. |
| 2004/0018042 | A1 | 1/2004 | Smith |
| 2004/0180412 | A1 | 9/2004 | Liu et al. |
| 2005/0025766 | A1 | 2/2005 | Liu et al. |
| 2005/0042669 | A1 | 2/2005 | Liu et al. |
| 2005/0142583 | A1 | 6/2005 | Liu et al. |
| 2005/0170376 | A1 | 8/2005 | Liu et al. |
| 2005/0227281 | A1 | 10/2005 | Liu et al. |
| 2005/0233381 | A1 | 10/2005 | Liu et al. |
| 2005/0281819 | A9 | 12/2005 | Liu et al. |
| 2006/0223086 | A1 | 10/2006 | Liu et al. |
| 2007/0066851 | A1 | 3/2007 | Liu et al. |

FOREIGN PATENT DOCUMENTS

| | | |
|---|---|---|
| EP | 0773227 | 5/1997 |
| WO | WO-9105058 | 4/1991 |
| WO | WO-9202536 | 2/1992 |
| WO | WO-9306121 | 4/1993 |
| WO | WO-0023458 | 4/2000 |
| WO | WO-0047775 | 8/2000 |
| WO | WO-02074929 | 9/2002 |
| WO | WO-02102820 | 12/2002 |
| WO | WO-02103008 | 12/2002 |

OTHER PUBLICATIONS

Alvarez, et al., "Photocleavable Protecting Groups as Nucleobase Protections Allowed the Solid-Phase Synthesis of Base-Sensitive SATE-Prooligonucleotides", *J. Org. Chem* (1999), 64, 6319-28.

Anderson, et al. "A Comparison of Selected mRNA and Protein Abundances in Human Liver" *Electrophiresis*, 18: 533-537, 1997.

Arap, et al., "Steps Toward Mapping the Human Vasculature by Phage Display", *Nat. Med.*, 2: 121-127, 2002.

Arnold, et al., "Design by Directed Evolution" *Acc. Chem. Res.* 31: 125-131, 1998.

Arnold, et al., "Directed Evolution of Biocatalysts" *Curr. Opin. Chem. Biol.* 3: 54-59, 1999.

Bain, et al., "Ribosome-Mediated Incorporation of a Non-Standard Amino Acid into a Peptide Through Expansion of the Genetic Code" *Nature* vol. 356, 1992, 537-539.

Ban, et al., "The Complete Atomic Structure of the Large Ribosomal Subunit at 2.4 Å Resolution" *Science*, 289: 905-920, 2000.

Bannwarth, et al., "A Simple and Effective Chemical Phosphyorylation Procedure for Biomolecules" *Helv. Chim. Acta*, 70: 175-186, 1987.

Becker, et al., "Synthesis, Sar and In Vivo Activity of Novel Thienopyridine Sulfonamide Pyrrolidinones as Factor Xa Inhibitors" *Bioorg. Med. Chem. Lett.* 9:2753-2758, 1999.

Berger, et al., "Universal Bases for Hybridization, Replication and Chain Termination", *Nucleic Acids Research*, 28, pp. 2911-2914, 2000.

Blanco, et al, "A Method for Detecting Protein-DNA Interactions at Sites of Chromatin Replication" *Analytical Biochemistry*, 163: 537-545, 1987.

Bogarad, et al., "A Hierarchical Approach to Protein Molecular Evolution" *Proc. Natl. Acad. Sci. USA*, 96: 2591-2595, 1999.

Bolli, et al., "Pyranosyl-RNA: Chiroselective Self-Assembly of Base Sequences by Ligative Oligomerization of Tetranucleotide-2'3'-Cyclophosphates (with a Commentary Concerning the Origin of Biomolecular Homochirality)" *Chem. Biol.* 4: 309-320, 1997.

Boschelli, et al., "Synthesis of Amphotericin B. 2. Fragment C-D of the Aglycone" *Tetrahedron Lett.* 26: 5239-5242, 1985.

Bostwick, et al.,"RPR120844, A Novel, Specific Inhibitor of Coagulation Factor Xa Inhibits Venous Thrombosis in the Rabbit" *Thromb Haemost*, 81: 157-160, 1999.

Brenner, et al,"Encoded Combinatorial Chemistry", *Proc. Natl. Acad. Sci.*, vol. 89, 5381-5383, 1992.

Brenner, et al., "In Vitro Cloning of Complex Mixtures of DNA on Microbeads: Physical Separation of Differentially Expressed cDNA's", *Proc. Natl. Acad. Sci. USA*, 97, 1665-1670, 2000.

Bresler, et al.,"Stability of Peptidyl-tRNA—The Intermediate of Protein Synthesis", *Biochimica et Biophysica Acta*, vol. 155: 465-475, 1968.

Breslow, et al., "Biomimetric Chemistry and Artificial Enzymes: Catalysis by Design." *Acc. Chem. Res.* 28: 146-153, 1995.

Brooks, et al., "Disruption of Angiogenesis by PEX, a Noncatalytic Metalloproteinase Fragment with Integrin Binding Activity", *Cell*, 92: 391-400, 1998.

Brooks, et al., "Antiintegrin αvβ$_3$ Blocks Human Breast Cancer Growth and Angiogenesis in Human Skin" *J. Clin. Invest*, 96: 1815-1822, 1995.

Brooks, et al., "Integrin αvβ$_3$ Antagonists Promote Tumor Regression by Inducing Apoptosis of Angiogenic Blood Vessels" *Cell*, 79: 1157-1164, 1994.

Bruick, et al., "Template-Directed Ligation of Peptides to Oligonucleotides" *Chem. Biol.* 3: 49-56, 1996.

Burrows, et al., "Oxidative Nucleobase Modifications Leading to Strand Scisson" *Chem. Rev.* 98: 1109-1152, 1998.

Böhler, et al., "Template Switching Between PNA and RNA Oligonucleotides" *Nature*, 376: 578-581, 1995.

Cadwell, et al., "Randomization of Genes by PCR Mutagenesis" *PCR Methods Appl.* 2:28-33, 1992.

Calderone, et al., "Directing Otherwise Incompatible Reactions in a Single Solution by Using DNA-Templated Organic Synthesis." *Angew. Chem. Int. Ed.* 41: 4104-8, 2002.

Celewicz, et al. (1998) Pol. J. Chem., 72: 725-734.

Chen, et al., "Template-Directed Synthesis on Oligodeoxycytidylate and Polydeoxycytidylate Templates" *J. Mol. Biol.* 181:271-279, 1985.

Cho, et al., "An Unnatural Biopolymer" *Science*, 261: 1303-1305, 1993.

Choi, et al., "Inhibition of Neointimal Hyperplasia by Blocking αvβ$_3$ Integrin with a Small Peptide Antagonist Gpen GRGDSPCA" *J. Vasc. Surg*, 19: 125-134, 1994.

Choi-Sledeski, et al., "Sulfonamidopyrrolidinone Factor Xa Inhibitors: Potency and Selectivity Enhancements via P-1 and P-4 Optimization" *J. Med. Chem.* 42: 3572-3587, 1999.

Collado, et al., "Diastereoselective Functionalization of 5-Hydroxy Prolinates by Tandem Horner-Emmons-Michael Reaction"*Tetrahedron Lett.* 35: 8037, 1994.

Compton, "Nucleic Acid Sequence-Based Amplification" *Nature*, 350: 91-92 (1991).

Corey, et al., *J. Org. Chem.* 51: 1925-1926, 1986.

(56) References Cited

OTHER PUBLICATIONS

Cotarca, et al., *Synthesis* 328-332, 1997.
Czlapinski, et al., "Nucleic Acid Template-Directed Assembly of Metallosalen-DNA Conjugates" *J. Am. Chem. Soc.* 123: 8618-8619, 2001.
Dahmen, et al., Synthesis-Stuttgart, 1431-1449, 2001.
Davis, "Intermediates in Amino Acid Biosynthesis" *Adv. Enzymol.* 16: 287-295, 1955.
Dechantsreiter, et al., "N-Methylated Cyclic RGD Peptides as Highly Active and Selective $\alpha v \beta_3$ Integrin Antagonists" *J. Med. Chem.* 42: 3033-3040, 1999.
Delia, et al., *Heterocycles* 35: 1397-1410, 1993.
Dewey, et al., "New Uridine Derivatives for Systematic Evolution of RNA Ligands by Exponential Enrichment", *J. Am. Chem. Soc.* vol. 117: 8474-8475, 1995.
Dietz, et al, "Photochemical Reduction of 5-Bromouracil by Cystine Derivatives and Coupling of 5-Bromouracil to Cystine Derivatives" *Photochemistry and Photobiology*, 49: 121-129, 1989.
Drews, J. "Drug Discovery: A Historical Perspective", *Science*, 287: 1960-1964, 2000.
Eaton, "The Joys of In Vitro Selection: Chemically Dressing Oligonucleotides to Satiate Protein Targets", *Current Opinion in Chemical Biology*, 1: 10-16, 1997.
Eliseev, et al., "Dynamic Combinatorial Chemistry: Evolutionary Formation and Screening of Moecular Libraries" *Combinatorial Chemistry in Biology*, 243: 159-172, 1999.
Ellis, et al., "Functional Analysis of the T-Cell Restricted Protein Tyrosine Kinase TxK", *Biochem. J.*, 335; 277-284, 1998.
Gocke, "Mechanism of Quinolone Mutagenicity in Bacteria" *Mutation Research*, 248: 135-143, 1991.
Evans, et al., "Proton-Activated Fluorescence As a Tool for Simultaneous Screening of Combinatorial Chemical Reactions." *Curr. Opin. Chem. Biol.* 6: 333-338, 2002.
Ewing, et al, "Design and Structure—Activity Relationships of Potent and Selective Inhibitors of Blood Coagulation Factor Xa" *J. Med. Chem.* 42: 3557-3571, 1999.
Famulok, et al. "Oligonucleotide Libraries-Variatio Delectat" *Curr. Opin. Chem. Biol.* 2:320-327, 1998.
Fenn and Herman, *Analytical Chemistry*, 1990, 190: 78-83.
Fleet, et al., "Enantiospecific Synthesis of Shikimic Acid from D-Mannose: Formation of a Chiral Cyclohexene by Intramolecular Olefination of a Carbohydrate-Derived Intermediate" *J. Chem. Soc. Perkins, Trans.* I: 905, 1984.
Fleischer, et al., "Conversion of Aliphatic and Alicyclic Polyalcohols to the Corresponding Primary Polyamines", *J. Org. Chem* 36, 3042-44, 1971.
Francis, et al., "Combinatorial Libraries of Transition-Metal Complexes, Catalysts and Materials" *Curr. Opin. Chem. Biol.* 2:422-428, 1998.
Francis, et al., "Discovery of Novel Catalysts for Alkene Epoxidation from Metal-Binding Combinatorial Libraries" *Angew. Chem. Int. Ed. Engl.* 38: 937-941, 1999.
Friedlander, et al., "Definition of Two Angiogenic Pathways by Distinct $\alpha v$ Integrins" *Science*, 270: 1500-1502, 1995.
Fruchart, et al., "A New Linker for the Synthesis of C-Terminal Peptide $\alpha$-oxo-Aldehydes" *Tetrahedron Lett.* 40: 6225, 1999.
Fruchtel, et al., "Organic Chemistry on Solid Supports" *Angew. Chem. Int. Ed. Engl.* 35: 17-42, 1996.
Gallop, et al., "Applications of Combinatorial Technologies to Drug Discovery, 1. Background and Peptide Combinatorial Libraries" *J. Med. Chem.* 37: 1233-1251, 1994.
Gartner, et al., "Expanding the Reaction Scope of DNA-Templated Synthesis." *Angew Chem. Int. Ed.* 41: 1796-1800, 2002.
Gartner, et al., "The Generality of DNA-Templated Synthesis as a Basis for Evolving Non-Natural Small Molecules" *J. Am. Chem. Soc.* 123: 6961-6963, 2001.
Gat, et al., "Reading DNA Differently" *Biopolymers*, 48: 19-28, 1998.
Gevorkian, et al. "Rapid Communication Identification of Autoimmune Thrombocytopenic Purpura-Related Epitopes using Phage-Display Peptide Library" *Clin. Immunol. Immunopathol*, 86: 305-309, 1998.
Geyer, et al., "Conformational Analysis of a Cyclic RGD Peptide Containing a $\Psi$ [$CH_2$—NH] Bond: A Positional Shift in Backbone Structure Caused by a Single Dipeptide Mimetic", *J. Am. Chem. Soc.* 116: 7735-7743, 1994.
Gilbertson, et al., "A Symmetric Catalysis with Libraries of Palladium $\beta$-Turn Phosphine Complexes" *J. Am. Chem. Soc.* 122: 6522-6523, 2000.
Gordon, et al., "Applications of Combinatorial Technologies to Drug Discovery. 2. Combinatorial Organic Synthesis, Library Screening Strategies, and Future Directions" *J. Med.Chem.* 37: 1385-1401, 1994.
Gourlain, et al., "Enhancing the Catalytic Repertoire of Nucleic Acids. II. Simultaneous Incorporation of Amino and Imidazolyl Functionalities by Two Modified Triphosphates During PCR" *Nucleic Acids Res.* 29: 1898-1905, 2001.
Gryaznov, et al., "Chemical Ligation of Oligonucleotides in the Presence and Absence of a Template", *J. Am. Chem. Soc.* 115: 3808-3809, 1993.
Gryaznov, et al., "Template Controlled Coupling and Recombination of Oligonucleotide Blocks Containing Thiophosphoryl Groups", *Nucleic Acids Research*, 21: 1403-1408, 1993.
Guatelli, et al. "Isothermal, In Vitro Amplification of Nucleic Acids by a Multienzyme Reaction Modeled After Retroviral Replication", *Proc. Natl. Acad, Sci.*, 87: 1874-1878, 1990.
Haaima, et al., "Peptide Nucleic Acids (PNAs) Containing Thymine Monomers Derived from Chiral Amino Acids: Hybridization and Solubility Properties of D-Lysine PNA" *Angew. Chem. Int. Ed. Engl.* 35: 1939-1942, 1996.
Haeuptle, et al., "Translation Arrest by Oligodeoxynucleotides Complementary to mRNA Coding Sequences Yields Polypeptides of Predetermined Length", *Nucleic Acids Research*, 14: 1427-1448, 1986.
Hamburger, et al.,"Peptidyl-tRNA XI. The Chemical Synthesis of Phenylalanine-Containing Oligopeptidyl-tRNA", *Biochimica et Biophysica Acta*, 213:115-123, 1970.
El-Dorry, *Biochimica et Biophysica Acta*, vol. 867, 1986, 252-255.
Haubner, et al., "Structural and Functional Aspects of RGD-Containing Cyclic Pentapeptides as Highly Potent and Selective Integrin $\alpha v \beta_3$ Antagonists" *J. Am. Chem. Soc.* 118: 7461-7472, 1996.
Heck, et al., "Palladium-Catalyzed Vinylation of Organic Halides" *Org. React.* 27: 345, 1982.
Herrera-Estrella, et al., "VirD Proteins of Agrobacterium Tumefaciens are Required for the Formation of a Covalent DNA-Protein Complex at the 5' Terminus of T-Strand Molecules", *The EMBO Journal*, 7: 4055-4062, 1988.
Herrlein, et al., "A Covalent Lock for Self-Assembled Oligonucleotide Conjugates" *J. Am. Chem. Soc.* 117:10151-10152, 1995.
Heywood, et al., *Biochemistry*, vol. 57, 1967, 1002-1009.
Heywood, et al., *Biochemistry*, vol. 7, 1968, 3289-3296.
Hirama, et al., "Asymmetric Induction in the Intramolecular Conjugate Addition of—or $\delta$—Carbamoyloxy—, ($\beta$-Unsaturated Esters. A New Method for Diastereoselective Amination and Divergent Synthesis of 3-Amino-2,3,6-Trideoxyhexoses" *Heterocycles*, 28: 1229-1247, 1989.
Hirama, et al., "Intramolecular Michael Addition of O-Carbamates to $\alpha,\beta$ Unsaturated Esters. A New Diastereoselective Amination in an Acyclic System" *J. Am. Chem. Soc.* 107: 1797-1798, 1985.
Hooper, et al., "Mode of Action of the New Quinolones: New Data" *Eur. J. Clin. Microbiol. Infect. Dis.*, 10: 223-231, 1991.
Houdebine, et al., "Purification of the mRNAs for Ewe $\alpha_s$-Casein and $\beta$-Casein by Immunoprecipitation of Polysomes", *Eur. J. Biochem.*, 63: 9-14, 1976.
House, et al., "The Chemistry of Carbanions. XVII. The Addition of Methyl Organometallic Reagents to Cyclohexenone Derivatives" *J. Org. Chem.* 33: 949, 1968.
Hughes, Application of Polymer-Bound Phosphonium Salts as Traceless Supports for Solid *Tetrahedron Lett.* 37: 7595-7598, 1996.

(56) References Cited

OTHER PUBLICATIONS

Hyrup, et al., "Peptide Nucleic Acids (PNA): Synthesis, Properties and Potential Applications", *Bioorganic & Medical Chemistry*, 4, 5-23, 1996.

Ijiro, et al., *J. Chem. Soc. Chem. Comm.*, 18:1339-1341, 1992.

Illuminati, et al., "Ring Closure Reactions of Bifunctional Chain Molecules" *Acc. Chem. Res.* 14: 95-102, 1981.

Inoue, et al., "Oligomerization of (Guanosine 5'-Phosphor)-2-Methylimidazolide on Poly(C): An RNA Polymerase Model" *J. Mol. Biol.* 162: 201-217, 1982.

Inoue, et al., "Substituent Control of the Poly (C)—Directed Oligomerization of Guanosine 5'—Phosphoroimidazolide" *J. Am. Chem. Soc.* 103: 7666-7667, 1981.

Inoue, et al., "Template-Directed Synthesis on the Pentanucleotide CpCpGpCpC" *Journal of Molecular Biology*, 178: 669-676, 1984.

International Search Report, PCT/US05/29294, mailed on Aug. 2, 2007.

Ito, et al. "Acetone-Sensitized Photocoupling of 5-Bromouridine to Tryptophan Derivatives via Electron-Transfer Process", *J. Amer. Chem. Soc.*, 102: 7535-7541, 1980.

Jemth, et al. "Kinetic Characterization of Recombinant Human Glutathione Transferase T1-1, A Polymorphic Detoxication Enzyme", *Arch. Biochem. Biophys.* 348: 247-54, 1997.

Johansson, et al., "Regioselective Reductive Ring-Opening of 4-Methoxybenzylidene Acetals of Hexopyranosides. Access to a Novel Protecting-Group Strategy. Part 1" *J. Chem. Soc. Perkins Trans*, I: 2371, 1984.

Johnson, et al., "Evidence for Posttranslational O-Glycosylation of Fetuin" *Biochemistry*, 25: 5518-5525, 1986.

Johnston, et al., "RNA-Catalyzed RNA Polymerization: Accurate and General RNA-Templated Primer Extension" *Science*, 1319-1325, 2001.

Jost, et al., "Quantitative Precipitation of Short Oligonucleotides with Low Concentrations of Cetyltrimethylammonium Bromide" *Nucleic Acids Res.* 17: 2143, 1989.

Joyce, et al., "Directed Evolution of Nucleic Acid Enzymes" *Annu. Rev. Biochem.* 73: 791-836, 2004.

Kanan, et al., *Nature*, 431(7008):545-549, 2004.

King, et al., "Bis (Dialkylamino) Phosphines" *J. Org. Chem.* 49: 1784-1789, 1984.

Kinoshita, et al., *Nucleic Acids Symposium Series*, vol. 34, 1995, 201-202.

Kohli, et al., Biomimetric Synthesis and Optimization of Cyclic Peptide Antibiotics. *Nature* 418: 658-61, 2002.

Kuntz, et al., "Combinatorial Catalyst Discovery" *Current Opinion in Chemical Biology*, 3: 313-319, 1999.

Kupsch, et al. "Isolation of Human Tumor-Specific Antibodies by Selection of an Antibody Phage Library on Melanoma Cells", *Clin Cancer Res.*, 5: 925-931, 1999.

Kusumoto, et al., *Bull. Chem. Soc. Jpn.* 59: 1296-1298, 1986.

Latham, et al., "The Application of a Modified Nucleotide in Aptamer Selection: Novel Thrombin Aptamers Containing 5-(Pentynyl)-2'—Deoxyuridine" *Nucleic Acids Res.* 22: 2817-2822, 1994.

Leadley, et al., "Pharmacodynamic Activity and Antithrombotic Efficacy of RPR120844, a Novel Inhibitor of Coagulation Factor Xa" *J. Cardiovasc. Pharmacol.* 34: 791-799, 1999.

Lee, et al.,"Enhancing the Catalytic Repertoire of Nucleic Acids: a Systematic Study of Linker Length and Rigidity" *Nucleic Acids Res.* 29: 1565-1573, 2001.

Leon, et al., "Covalent Coupling of 4-Thiouridine in the Initiator Methionine tRNA to Specific Lysine Residues in *Escherichia coli* Methionyl-tRNA Synthetase", *Biochemistry*, 26: 7113-7121, 1987.

Li, et al., "A Catalytic DNA for Porphyrin Metallation" *Nat. Struct. Biol.*, 3:743-747, 1996.

Li, et al., "Capping DNA with DNA" *Biochemistry*, 39: 3106-3114, 2000.

Li, et al., "Chemical Self-Replication of Palindromic Duplex DNA" *Nature*, 369: 218-221, 1994.

Li, et al., "DNA-Catalyzed Polymerization" *J. Am. Chem. Soc.* 124: 746-747, 2002.

Li, et al., "Phosphorylating DNA with DNA" *Proc. Natl. Acad. Sci. USA*, 96: 2746-2751, 1999.

Li, et al., "Stereoselectivity in DNA-Templated Organic Synthesis and Its Origins." *J. Am. Chem. Soc.* 125: 10188-9, 2003.

Li, et al., "Toward an Efficient DNAzyme" *Biochemistry*, 36:5589-5599, 1997.

Li, et al., *Angew. Chem. Int. Ed.*, VCH Verlag, Weinheim, DE, 43(37):4848-4870, 2004.

Lin, et al., "Formation of an Amino-Acid-Binding Pocket Through Adaptive Zippering-Up of a Large DNA Hairpin Loop" *Chem. Biol.* 5:555-572, 1998.

Lin, et al., "Structural Basis of DNA Folding and Recognition in an AMP-DNA Aptamer Complex: Distinct Architectures But Common Recognition Motifs for DNA and RNA Aptamers Complexed to AMP" *Chem. Biol.* 4: 817-832, 1997.

Gartner, et al., *J. Am. Chem. Soc.* 123: 6961, 2001.

Liu, et al., "Generating New Molecular Function: A Lesson from Nature" *Angew. Chem. Intl. Ed. Eng.* 38:37-54, 1999.

Lober, et al., "Palladium-Catalyzed Hydroamination of 1,3-Dienes: A Coloimetric Assay and Enantioselective Additions." *J. Am. Chem. Soc.* 123: 4366-7, 2001.

Luther, et al., "Surface-Promoted Replication and Exponential Amplification of DNA Analogues" *Nature*, 396: 245-248, 1998.

Lynn, et al., "Living Ring-Opening Methathesis Polymerization in Water" *J. Am. Chem. Soc.*, 12: 1627-1628, 1998.

Lynn, et al., "Water-Soluble Ruthenium Alkylidenes: Synthesis, Characterization, and Application to Olefin Metathesis in Protic Solvents" *J. Am. Chem. Soc.* 122: 6601-6609, 2000.

MacLean, et al., "Encoded Combinatorial Chemistry: Synthesis and Screening of a Library of Highly Functionalized Pyrrolidines", *Proc. Natl. Acad. Sci. USA*, 94: 2805-2810, 1997.

Magid, "Nucleophilic and Organometallic Displacement Reactions of Allylic Compounds: Stereo—and Regiochemistry" *Tetrahedron*, 36: 1901, 1980.

Mahal, et al., "Engineering Chemical Reactivity on Cell Surfaces Through Oligosaccharide Biosynthesis" *Science*, 276: 1125-1128, 1997.

Maignan, et al., "Crystal Structures of Human Factor Xa Complexed with Potent Inhibitors" *J. Med. Chem.* 43: 3226-3232, 2000.

Marks et al., "Molecular Evolution of Proteins on Filamentous Phage", *J. Biol. Chem.*, 267: 16007-16010, 1992.

Marlowe, et al.,"Design, Synthesis and Structure-Activity Relationship of a Series of Arginine Aldehyde Factor Xa Inhibitors. Part 1: Structures Based on the (D)-Arg-Gly-Arg Tripeptide Sequence" *Bioorg. Med. Chem. Lett.* 10 (13-16): 2000.

Mattheakis, et al. "An In Vitro Polysome Display System for Identifying Ligands from Very Large Peptide Libraries", *Proc. Natl. Acad. Sci.*, 91: 9022-9026, 1994.

Mel'nikov, et al., "Solubilization of DNA-Cationic Lipid Complexes in Hydrophobic Solvents. A Single-Molecule Visualization by Fluorescence Microscopy" *Langmuir*, 15: 1923-1928, 1999.

Minshull, et al., "Protein Evolution by Molecular Breeding" *Curr Opin. Chem. Biol.* 3: 284-290, 1999.

Miyaura, et al., "Palladium-Catalyzed Cross-Coupling Reactions of Organoboron Compounds." *Chem. Rev.* 95: 2457-2483, 1995.

Mohr, et al., "Synthesis of Water-Soluble, Aliphatic Phoshines and Their Application to Well-Defined Ruthenium Olefin Metathesis Catalysts" *Organometallics*, 15: 4317-4325, 1996.

Muth, et al., "A Single Adenosine with a Neutral $pK_a$ in the Ribosomal Peptidyl Transferase Center" *Science*, 289: 947-950, 2000.

Nagasaka, et al., "Wittig Reactions of 1-Alkoxycarbonyl-2-Hydroxypyrrolidines and—Piperidines: Synthesis of (±)—Hygrine and (±) -2-Epilasubine II" *Heterocycles*, 29: 155, 1989.

Nakano, et al.,"General Acid-Base Catalysis in the Mechanism of a Hepatitis Delta Virus Ribozyme" *Science*, 287: 1493-1497, 2000.

Nissen, et al., "The Structural Basis of Ribosome Activity in Peptide Bond Synthesis" *Science*, 289: 920-930, 2000.

Nolte, et al., Mirror-Design of L-Oligonucleotide Ligands Binding to L- *Nature Biotechnol*, 14: 1116-1121, 1996.

Norris, et al. "Mechanistic Studies of the 5-Iodouracil Chromophore Relevant to Its Use in Nucleoprotein Photo-Cross-Linking" *J. Amer. Chem. Soc.* 118: 5769-5803, 1996.

(56) References Cited

OTHER PUBLICATIONS

Olofson, et al., "Selective N-Dealkylation of Teritiary Amines with Vinyl Chloroformate: An Improved Synthesis of Naloxone" *Tetrahedron Lett.* 18: 1567-1570, 1977.
Olofson, et al., "Use of the Vinyloxycarbonyl Group for Amino Protection in Peptide Synthesis" *Tetrahedron Lett.*, 18: 1563-1566, 1977.
Olofson, et al., "Value of the Vinyloxycarbonyl Unit in Hydroxyl Protection: Application to the Synthesis of Nalorphine" *Tetrahedron Lett.* 18: 1571-1574, 1977.
Orgel, et al., "Unnatural Selection in Chemical Systems" *Acc. Chem. Res.* 28:109-118, 1995.
Pagratis, et al. "Potent 2'-Amino-, and 2'-Fluoro-2'—Deoxyribonucleotide RNA Inhibitors of Keratinocyte Growth Factor", (1997) *Nature Biotechnol*, 15: 68-72.
Pasqualini, et al. (1996), *Nature*, 380: 364-366.
Pasqualini, et al."Aminopeptidase N is a Receptor for Tumor-Homing Peptides and a Target for Inhibiting Angiogenesis", *Cancer Res.*, 60: 722-727, 2000.
Pawlas, et al., *J. Am. Chem. Soc.*, 124:3669-3679, 2002.
Pedersen, et al., (1998) *PNAS.* 18: 10523-10528.
Perrin, et al., "Bridging the Gap Between Proteins and Nucleic Acids: A Metal-Independent RNAseA Mimic with Two Protein-Like Functionalities" *J. Am. Chem. Soc.*, 123: 1556-1563, 2001.
Perrin, et al.,"Expanding the Catalytic Repertoire of Nucleic Acid Catalysts: Simultaneous Incorporation of Two Modified Deoxyribonucleoside Triphosphates Bearing Ammonium and Imidazolyl Functionalities" *Nucleosides Nucleotides*, 18: 377-391, 1999.
Pfaff, et al., "Selective Recognition of Cyclic RGD Peptides of NMR Defined Conformation of αIIbβ3, α5β1 Integrins" *J. Biol. Chem.* 269: 20233-20238, 1994.
Polacek, et al., "Ribosomal Peptidyl Transferase can Withstand Mutations at the Putative Catalytic Nucleotide" *Nature*, 411: 498-501, 2001.
Püschl, et al., "Peptide Nucleic Acids (PNAs) with a Functional Backgone" *Tetrahedron Lett.* 39: 4707-4710, 1998.
Rai, et al., "Development of Potent and Selective Factor Xa Inhibitors" *Bioorg. Med. Chem. Lett*, 11: 1797-1800, 2001.
Reetz, et al., "Combinatorial and Evolution-Based Methods in the Creation of Anantioselective Catalysts" *Angew. Chem. Int. Ed.* 40: 284-310, 2001.
Rembold, et al., "Single-Strand Regions of Poly(G) Act as Templates for Oligo(C) Synthesis" *J. Mol. Evol.* 38:205-210, 1994.
Roberts, et al. "RNA-Peptide Fusions for the In Vitro Selection of Peptides and Proteins" *Proc. Natl. Acad. Sci.*, 94: 12297-302, 1997.
Rodriguez, et al., "Template-Directed Extension of a Guanosine 5'-Phosphate Covalently Attached to an Oligodeoxycytidylate Template" *J. Mol. Evol.* 33: 477-482, 1991.
Rosenbaum, et al., "Efficient and Sequence-Specific DNA-Templated Polymerization of Peptide Nucleic Acid Aldehydes." *J. Am. Chem. Soc.* 125: 13924-5, 2003.
Rostovtsev, et al., "A Stepwise Huisgen Cycloaddition Process: Copper(I)-Catalyzed Regioselective 'Ligation' of Azides and Terminal Alkynes." *Angew. Chem. Int. Ed.* 41: 2596-9, 2002.
Saiki, et al. "Enzymatic Amplification of β-Globin Genomic Sequences and Restriction Site Analysis for Diagnosis of Sickle Cell Anemia" *Science*, 230: 1350-1354, 1985.
Sakthievel, et al.,"Expanding the Potential of DNA for Binding and Catalysis: Highly Functionalized dUTP Derivative thatare Substrates for Thermostable DNA Polymerases" *Angew. Chem. Int. Ed.*, 37: 2872-2875, 1998.
Santoro, et al., "A General Purpose RNA-Cleaving DNA Enzyme" *Proc. Natl. Acad. Sci. USA*, 94: 4262-4266, 1997.
Saxon, et al., "A "Traceless" Staudinger Ligation for the Chemoselective Synthesis of Amide Bonds", *Organic Letters*, 2, pp. 2141-2143, 2000.
Scharf, et al. "Direct Cloning and Sequence Analysis of Enzymatically Amplified Genomic Sequences", *Science*, 233: 1076-1078, 1986.

Scheffer, et al., "Selection and Characterisation of a Phage-Displayed Human Anibody (Fab) Reactive to the Lung Resistance-Related Major Vault Protein", *Br J. Cancer*, 86: 954-962, 2002.
Schmidt, et al., "Information Transfer from DNA to Peptide Nucleic Acids by Template-Directed Syntheses" *Nucleic Acids Research*, 25, 4792-4796, 1997.
Schmidt-Dannert, et al., "Directed Evolution of Industrial Enzymes" *Trends Biotechnol.* 17: 135-136, 1999.
Scholl, et al., "Synthesis and Activity of a New Generation of Ruthenium-Based Olefin Metathesis Catalysts Coordinated with 1,3-Dimesityl-4,5-Dihydroimidazol-2-Ylidene Ligands" *Org. Lett.* 1(6):953, 1999.
Schultz, et al.,. "Completing the Circle." *Nature* 418: 485, 2002.
Schultze, et al., Three-Dimensional Solution Structure of the Thrombin-Binding DNA Aptamer d(GGTTGGTGTGGTTGG) *J. Mol. Biol.* 235: 1532-1547, 1994.
Schwartz, et al., "Template-Directed Synthesis of Novel, Nucleic Acid-Like Structures" *Science*, 228: 585-587, 1985.
Scott, "How Were Porphyrins and Lipids Synthesized in the RNA World?" *Tetrahedron Lett.* 38: 4961-4964, 1997.
Seeberger, et al., "Solid-Phase Oligosaccharide Synthesis and Combinatorial Carbohydrate Libraries" *Chem Rev.* 100, 4349-4393, 2000.
Seela, et al., "Oligonucleotides Containing 7-Deazaadenines: The Influence of the 7-Substituent Chain Length and Charge on the Duplex Stability" *Helv. Chem. Acta*, 82:1878-1898, 1999.
Seela, et al., "Palladium-Catalyzed Cross Coupling of 7-Iodo-2' Deoxytubercidin with Terminal Alkynes" *Synthesis* 726-730, 1996.
Shao, et al., "Random-Priming in Vitro Recombination: An Effective Tool for Directed Evolution" *Nucleic Acids Research*, 26(2): 681-83, 1998.
Sheppard, et al., "A DNA Enzyme with N-Glycosylase Activity" *Proc. Natl. Acad. Sci. USA*, 97: 7802-7807, 2000.
Shimizu, et al., *Angew Chem. Int. Ed.*, 36: 1997.
Shishido,et al., "1,2-Asymmetric Induction in Intramolecular Michael Reaction. A Novel and Enantioselective Route to (+) Geissman Lactone" *J. Chem. Soc. Perkins Trans*, I: 993-1004, 1987.
Siegel, et al. "Isolation of Cell Surface-Specific Human Monoclonal Antibodies Using Phage Display and Magnetically-Activated Cell Sorting: Applications in Immunohematology" *J. Immunol. Methods*, 206: 73-85, 1997.
Smidt, et al., *Angew Chem* 74: 93-102, 1962.
Smidt, et al., *Angew. Chem.* 71: 176-182, 1959.
Smith, G., "Filamentous Fusion Phage: Novel Expression Vectors That Display Cloned Antigens on the Virion Surface" *Science*, 228: 1315-1317, 1985.
Smith, G., "The Progeny of Sexual PCR" *Nature*, 370: 324-325, 1994.
Soumillion, et al., "Selection of β-Lactamase on Filamentous Bacteriophage by Catalytic Activity", *J. Mol. Biol.* 237: 415-22, 1994.
Stambuli, et al., "Recent Advances in the Discovery of Organometallic Catalysts Using High-Throughput Screening Assays" *Curr. Opin. Chem. Biol.* 7: 420-426, 2003.
Stambuli, et al., "Screening of homogenous Catalysts by Fluorescence Resonance Energy Transfer. Identification of Catalysts for Room-Temperature Heck Reactions." *J. Am. Chem. Soc.* 123: 2677-8, 2001.
Staunton, et al., "Polyketide Biosynthesis: A Millennium Review." *Nat. Prod. Rep.* 18: 380-416, 2001.
Stemmer, "DNA Shuffling by Random Fragmentation and Reassembly: In Vitro Recombination for Molecular Evolution" *Proc. Natl. Acad. Sci.USA*, 91: 10747-10751, 1994.
Stemmer, W., "Rapid Evolution of a Protein in Vitro by DNA Shuffling" *Nature*, 370: 389-391, 1994.
Still, et al., "Chemical Consequences of Conformation in Macrocyclic Compounds" *Tetrahedron*, 37: 3981-3996, 1981.
Sutherlin, et al., "Stereoselective Synthesis of Dipyranyl C-Disaccharides" *Tetrahedron Lett.* 34: 4897, 1993.
Tamura, et al., "Oligonucleotide-Directed Peptide Synthesis in a Ribosome- and Ribozyme-Free System" *Proc. Natl. Acad. Sci USA*, 98: 1393-1397, 2001.
Tanaka, et al., J. Am. Chem. Soc., 118:10679-10683, 1996.

(56) References Cited

OTHER PUBLICATIONS

Tarasow, et al., "Dressed for Success: Realizing the Catalytic Potential of RNA" *Biopolymers*, 48: 29-37, 1998.
Taylor, et al, "Thermographic Selection of Effective Catalysts From an Encoded Polymer-Bound Library." *Science* 280: 267-70, 1998.
Tseng-Law, et al. "Identification of a Peptide Directed Against the Anti-CD34 Antibody, 9C5, by Phage Display and Its Use in Hematopoietic Stem Cell Selection", *Exp. Hematol*, 27: 936-945, 1999.
Uhlmann, et al., "Synthesis and Properties of PNA/DNA Chimeras" *Angew. Chem. Int. Ed. Engl.* 35: 2632-2635, 1996.
Vacca, et al., "New Advances in the Discovery of Thrombin and Factor Xa Inhibitors" *Curr. Opin. Chem. Biol.*, 4: 394-400, 2000.
Gyllensten, et al., *PNAS*, 85: 7652-7656 (1988).
Varner, et al., "Review: $\alpha v \beta_3$: Angiogenesis and Apoptosis" The Integrin *Cell Adhes Commun*, 3: 367-374, 1995.
Visscher, J.et al., "Template-Directed Synthesis of Acyclic Oligonucleotide Analogs" *Journal of Molecular Evolution* 28, 3-6, 1988.
Wadsworth, et al., "Utility of Phosphate Carbanions in Olefin Synthesis" *J. Am. Chem.* 83: 1733-8, 1961.
Wang, et al., "Bioconjugation by Copper(I)-Catalyzed Azide-Alkyne [3+2] Cycloaddition." *J. Am. Chem. Soc.* 125: 3192-3, 2003.
Wells & Lowman. "Rapid Evolution of Peptide and Protein Binding Properties in Vitro" *Curr. Op. Struct. Biol.*, 2, 597-604, 1992.
Wennemers, Combinatorial Chemistry & High Throughput Screening, 4:273-285, 2001.
Wermuth, et al., "Stereoisomerism and Biological Activity of the Selective and Superactive $\alpha v \beta_3$ Integrin Inhibitor Cyclo (-RGDfV -) and Its Retro-Inverso Peptide" *J. Am. Chem. Soc.* 119: 1328-1335, 1997.
Wiegand, et al., "Selection of RNA Amide Synthases" *Chemistry and Biology*, 4: 675-683, 1997.
Wilson, et al., "In Vitro Selection of Functional Nucleic Acids." *Annu. Rev. Biochem.* 68: 611-647, 1999.
Winter, et al. "Making Antibodies by Phage Display Technology", *Annu. Rev. Immunol*, 12: 433-455, 1994.
Woodward, et al., "Asymmetric Total Synthesis of Erythromycin. 1. Synthesis of an Erythronolide a Seco Acid Derivative via Asymmetric Induction" *J. Am. Chem. Soc.*, 103: 3210-3213, 1981.
Written Opinion of the International Searching Authority, PCT/US05/29294, mailed on Aug. 2, 2007.
Xu, et al., "Nonenzymatic Autoligation in Direct Three-Color Detection of RNA and DNA Point Mutations" *Nat Biotechnol*, 19: 148-152, 2001.
Xu, et al., "Rapid and Selective Selenium-Mediated Autoligation of DNA Strands" *J. Am. Chem. Soc.*, 122: 9040-9041, 2000.
Zarling, et al., "Mapping of Lymphocyte Surface Polypeptide Antigens by Chemical Cross-Linking Linking with Bsocoes" *J. Immunology*, 124: 913-920, 1980.
Zhang, et al., "Lactone and Lactam Library Synthesis by Silver Ion-Assisted Orthogonal Cyclization of Unprotected Peptides" *J. Am. Chem. Soc.* 121: 3311-3320, 1999.
Zhao, et al., "A Methodological Comparison: The Advantage of Phosphorimidates in Expanding the Sugar Nucleotide Repertoire", *J. Org. Chem.* 63, 7568-7572, 1998.
Zhao, et al., "Molecular Evolution by Staggered Extension Process (StEP) in Vitro Recombination", *Nat. Biotechnol*, 16(3): 258-61, 1998.
Zhao, et al.,"Optimization of DNA Shuffling for High Fidelity Recombination", *Nucleic Acids Research*, 25(6): 1307-1308, 1997.
Pirrung et al., J. Org. Chem. (1998), 63, 241-46.

Labeled Components I

| Oligo ID | DNA Sequence (5'-->3') | 1/epsilon | mass (no 5'A*p) | expected mass (with 5'A*p) | w/ SM | MALDI data |
|---|---|---|---|---|---|---|
| generalized | pA*TCCGCAG-(ANx)-CACACC | | | | | |
| B-AN1-8b | pA*TCCGCAGAACTTCCTCTCGGGACACACC | 3.172 | 9056.9 | 9562.26 | 119.03 | 9679 |
| | | | | | 9681.29 | |
| B-AN2-8b | pA*TCCGCAGACGCGATGTTTCGACCACACC | 3.122 | 9096.9 | 9602.26 | 133.03 | 9741 |
| | | | | | 9735.29 | |
| B-AN3-8b | pA*TCCGCAGAGCGTTATGGTCCGACACACC | 3.075 | 9137 | 9642.36 | 145.09 | 9789 |
| | | | | | 9787.45 | |
| B-AN4-8b | pA*TCCGCAGACATGAGCCCACTACACACC | 3.087 | 9034.9 | 9540.26 | 127.08 | 9670 |
| | | | | | 9667.34 | |
| B-AN5-8b | pA*TCCGCAGCCACTGTTACTAGGGCACACC | 3.122 | 9096.9 | 9602.26 | 97.07 | 9701 |
| | | | | | 9699.33 | |
| B-AN6-8b | pA*TCCGCAGCGTGCTTGAGGAGAACACACC | 2.968 | 9186 | 9691.36 | 149.06 | 9841 |
| | | | | | 9840.42 | |
| B-AN7-8b | pA*TCCGCAGAGGCCTCTTAGACCCACACACC | 3.172 | 9056.9 | 9562.26 | 112.05 | 9675 |
| | | | | | 9674.31 | |
| B-AN8-8b | pA*TCCGCAGCTTAGTTTCGGCCACCACACC | 3.241 | 9047.9 | 9553.26 | 152.11 | 9704 |
| | | | | | 9705.37 | |
| B-AN9-8b | pA*TCCGCAGGAGGGTGATGCATGTCACACACC | 2.984 | 9217 | 9722.36 | 157.05 | 9870 |
| | | | | | 9879.41 | |
| B-AN10-8b | pA*TCCGCAGGCTGGACTAGTACACACACC | 3.058 | 9105.9 | 9611.26 | 83.05 | 9703 |
| | | | | | 9694.31 | |
| B-AN11-8b | pA*TCCGCAGTAGACACGCATGTGCCACACC | 2.983 | 9105.9 | 9611.26 | 115.08 | 9728 |
| | | | | | 9726.34 | |
| B-AN12-8b | pA*TCCGCAGTCGGACTTTGATGGCCACACC | 3.141 | 9128 | 9633.36 | 0 | 9627 |
| | | | | | 9633.36 | |
| B-AN13-8b | pA*TCCGCAGACCGAAGGGCAATACCACACC | 2.935 | 9124 | 9629.36 | 109.06 | 9735 |
| | | | | | 9738.42 | |
| B-AN14-8b | pA*TCCGCAGGTAAGCCCTTGGTATCACACC | 3.109 | 9112 | 9617.36 | 116.06 | 9725 |
| | | | | | 9733.42 | |

B-oligos labeled with pool B material B1-B14

Figure 10

Figure 11
Labeled Components II

| Oligo ID | DNA Sequence (5'-->3') | 1/epsilon | mass (no 5'A*p) | expected mass (with 5'A*p) | w/ SM | MALDI data |
|---|---|---|---|---|---|---|
| generalized | pA*TCCGCAG-(ANx)-CACACAGC | | | | | |
| B-ANself-8b A1 | pA*TCCGCAGTTGATGACCAGGCCACACAGC | 3.058 | 9105.9 | 9611.26 | 99.08 9710.34 | 9711 |
| B-ANself-8b A2 | pA*TCCGCAGTTGATGACCAGGCCACACAGC | 3.058 | 9105.9 | 9611.26 | 196.96 9808.22 | 9813 |
| B-ANself-8b A3 | pA*TCCGCAGTTGATGACCAGGCCACACAGC | 3.058 | 9105.9 | 9611.26 | 69.03 9680.29 | 9690 |
| B-ANself-8b A4 | pA*TCCGCAGTTGATGACCAGGCCACACAGC | 3.058 | 9105.9 | 9611.26 | 83.05 9694.31 | 9686 |
| B-ANself-8b A5 | pA*TCCGCAGTTGATGACCAGGCCACACAGC | 3.058 | 9105.9 | 9611.26 | 109.06 9720.32 | 9717 |
| B-ANself-8b A6 | pA*TCCGCAGTTGATGACCAGGCCACACAGC | 3.058 | 9105.9 | 9611.26 | 119.05 9730.31 | 9727 |
| B-ANself-8b A7 | pA*TCCGCAGTTGATGACCAGGCCACACAGC | 3.058 | 9105.9 | 9611.26 | 230.93 9842.19 | 9840 |
| B-ANself-8b A8 | pA*TCCGCAGTTGATGACCAGGCCACACAGC | 3.058 | 9105.9 | 9611.26 | 123.04 9734.3 | 9729 |
| B-ANself-8b A9 | pA*TCCGCAGTTGATGACCAGGCCACACAGC | 3.058 | 9105.9 | 9611.26 | 144.04 9755.3 | 9746 |
| B-ANself-8b A10 | pA*TCCGCAGTTGATGACCAGGCCACACAGC | 3.058 | 9105.9 | 9611.26 | 157.09 9768.35 | 9763 |
| B-ANself-8b A11 | pA*TCCGCAGTTGATGACCAGGCCACACAGC | 3.058 | 9105.9 | 9611.26 | 143.07 9754.33 | 9754 |
| B-ANself-8b A12 | pA*TCCGCAGTTGATGACCAGGCCACACAGC | 3.058 | 9105.9 | 9611.26 | 127.08 9738.34 | 9736 |
| B-ANself-8b A13 | pA*TCCGCAGTTGATGACCAGGCCACACAGC | 3.058 | 9105.9 | 9611.26 | 134.06 9745.32 | 9743 |
| B-ANself-8b A14 | pA*TCCGCAGTTGATGACCAGGCCACACAGC | 3.058 | 9105.9 | 9611.26 | 112.08 9723.34 | 9725 |

B-oligos labeled with pool A material-A1-A14 (for pool $A_{self}$)

Labeled Components III

| Oligo ID | DNA Sequence (5'-->3') | 1/epsilon mass | expected mass (no 5'link) | w/ SM (w/ 5'linker) | MALDI data |
|---|---|---|---|---|---|
| A1oligo | NH2--biotin--C6S-SC6--TTGAT | 19.08 | 1493.1 | 2422.38 | 99.08 | |
| A2oligo | NH2--biotin--C6S-SC6--TTGAT | 19.08 | 1493.1 | 2422.38 | 2521.46 | 2522.7 |
| A3oligo | NH2--biotin--C6S-SC6--TTGAT | 19.08 | 1493.1 | 2422.38 | 196.96 | |
| | | | | | 2619.34 | 2621.7 |
| A4oligo | NH2--biotin--C6S-SC6--TTGAT | 19.08 | 1493.1 | 2422.38 | 69.03 | |
| | | | | | 2491.41 | 2507.5 |
| A5oligo | NH2--biotin--C6S-SC6--TTGAT | 19.08 | 1493.1 | 2422.38 | 83.05 | |
| | | | | | 2505.43 | 2508.8 |
| A6oligo | NH2--biotin--C6S-SC6--TTGAT | 19.08 | 1493.1 | 2422.38 | 109.06 | |
| | | | | | 2531.44 | 2532.7 |
| A7oligo | NH2--biotin--C6S-SC6--TTGAT | 19.08 | 1493.1 | 2422.38 | 119.05 | |
| | | | | | 2541.43 | 2545.7 |
| A8oligo | NH2--biotin--C6S-SC6--TTGAT | 19.08 | 1493.1 | 2422.38 | 230.93 | |
| | | | | | 2653.31 | 2654 |
| A9oligo | NH2--biotin--C6S-SC6--TTGAT | 19.08 | 1493.1 | 2422.38 | 123.04 | |
| | | | | | 2545.42 | 2547.3 |
| A10oligo | NH2--biotin--C6S-SC6--TTGAT | 19.08 | 1493.1 | 2422.38 | 144.04 | |
| | | | | | 2566.42 | 2568 |
| A11oligo | NH2--biotin--C6S-SC6--TTGAT | 19.08 | 1493.1 | 2422.38 | 157.09 | |
| | | | | | 2579.47 | 2579 |
| A12oligo | NH2--biotin--C6S-SC6--TTGAT | 19.08 | 1493.1 | 2422.38 | 143.07 | |
| | | | | | 2565.45 | 2567.1 |
| A13oligo | NH2--biotin--C6S-SC6--TTGAT | 19.08 | 1493.1 | 2422.38 | 127.08 | |
| | | | | | 2549.46 | 2552.4 |
| A14oligo | NH2--biotin--C6S-SC6--TTGAT | 19.08 | 1493.1 | 2422.38 | 134.06 | |
| | | | | | 2556.44 | 2560.7 |
| | | | | | 112.08 | |
| | | | | | 2534.46 | 2532.3 |

A-oligos labeled with pool A material

Figure 12

Figure 13
Labeled Components IV

| Oligo ID | DNA Sequence (5'—>3') | 1/epsilon mass (no 5'link) | expected mass w/ 5'linker | w/ SM | MALDI data |
|---|---|---|---|---|---|
| AselfB1 | NH2--biotin--C6S-SC6--TTGAT | 19.08 | 1493.1 | 2422.38 | 119.03 | |
| | | | | | 2541.41 | 2540 |
| AselfB2 | NH2--biotin--C6S-SC6--TTGAT | 19.08 | 1493.1 | 2422.38 | 133.03 | |
| | | | | | 2555.41 | 2554.7 |
| AselfB3 | NH2--biotin--C6S-SC6--TTGAT | 19.08 | 1493.1 | 2422.38 | 145.09 | |
| | | | | | 2567.47 | 2567 |
| AselfB4 | NH2--biotin--C6S-SC6--TTGAT | 19.08 | 1493.1 | 2422.38 | 127.08 | |
| | | | | | 2549.46 | 2547 |
| AselfB5 | NH2--biotin--C6S-SC6--TTGAT | 19.08 | 1493.1 | 2422.38 | 97.07 | |
| | | | | | 2519.45 | 2518 |
| AselfB6 | NH2--biotin--C6S-SC6--TTGAT | 19.08 | 1493.1 | 2422.38 | 149.06 | |
| | | | | | 2571.44 | 2570.2 |
| AselfB7 | NH2--biotin--C6S-SC6--TTGAT | 19.08 | 1493.1 | 2422.38 | 112.05 | |
| | | | | | 2534.43 | 2533.7 |
| AselfB8 | NH2--biotin--C6S-SC6--TTGAT | 19.08 | 1493.1 | 2422.38 | 152.11 | |
| | | | | | 2574.49 | 2574 |
| AselfB9 | NH2--biotin--C6S-SC6--TTGAT | 19.08 | 1493.1 | 2422.38 | 157.05 | |
| | | | | | 2579.43 | 2580 |
| AselfB10 | NH2--biotin--C6S-SC6--TTGAT | 19.08 | 1493.1 | 2422.38 | 83.05 | |
| | | | | | 2505.43 | 2502 |
| AselfB11 | NH2--biotin--C6S-SC6--TTGAT | 19.08 | 1493.1 | 2422.38 | 115.08 | |
| | | | | | 2537.46 | 2532 |
| AselfB12 | NH2--biotin--C6S-SC6--TTGAT | 19.08 | 1493.1 | 2422.38 | 0 | |
| | | | | | 2422.38 | 2423 |
| AselfB13 | NH2--biotin--C6S-SC6--TTGAT | 19.08 | 1493.1 | 2422.38 | 109.06 | |
| | | | | | 2531.44 | 2531.3 |
| AselfB14 | NH2--biotin--C6S-SC6--TTGAT | 19.08 | 1493.1 | 2422.38 | 116.06 | |
| | | | | | 2538.44 | 2540 |

A-oligos labeled with pool B material (for $B_{self}$ pool)

Matrix Assembly Trials

Microarray Technology

DNA Microarrays have been printed with amino-terminated oligos on aldehyde silane slides (Nexterion slide-AL).

Features correspond to each $A_m \times B_n$ encoding oligo (14X14=196) as well as each homocoupling combination (28) and an internal standard (1) 196+28+1 = 225 = 15X15

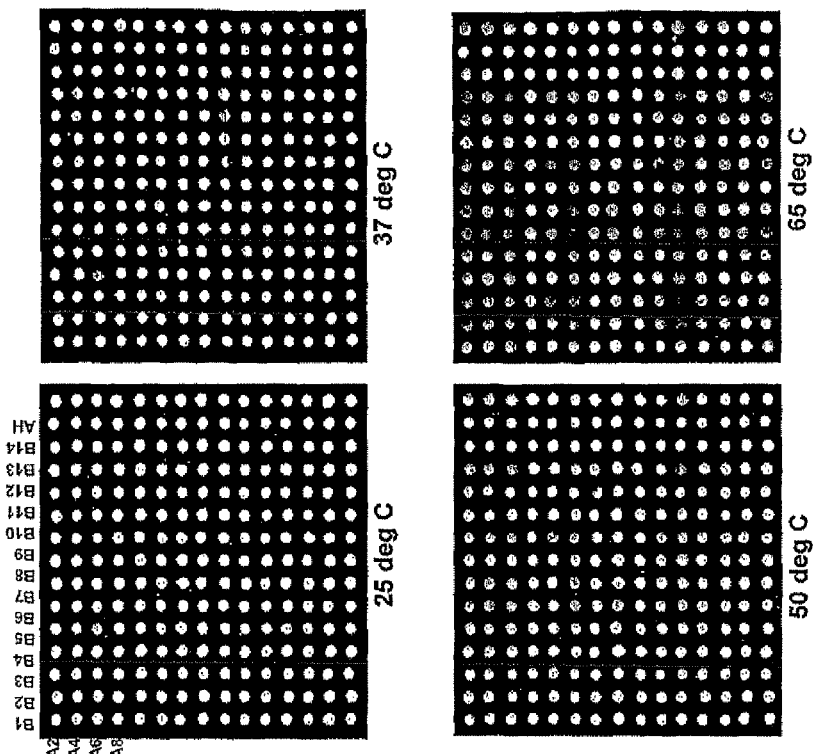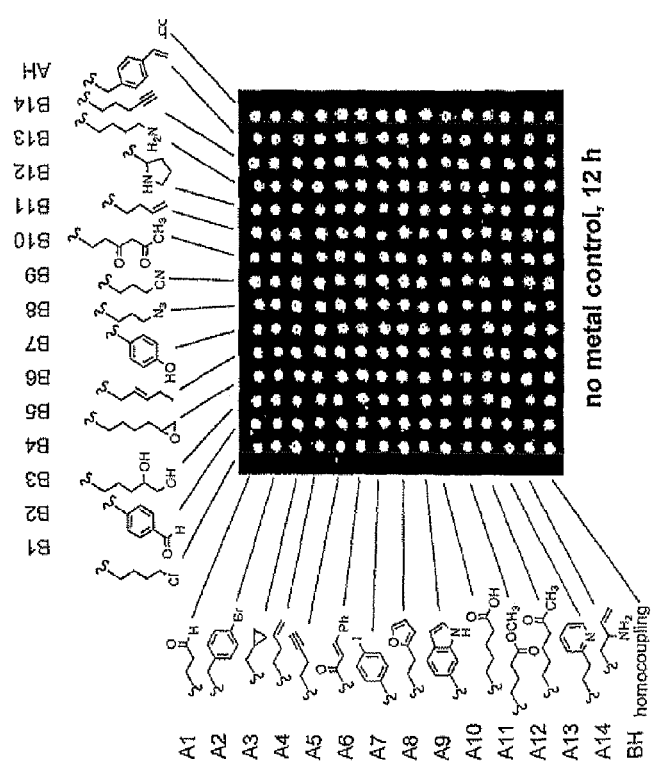
Figure 20

REACTION DISCOVERY SYSTEM

RELATED APPLICATIONS

The present application claims priority under 35 U.S.C. §119(e) to U.S. provisional patent application, U.S. Ser. No. 60/699,735, filed Jul. 15, 2005, incorporated herein by reference.

GOVERNMENT SUPPORT

The work described herein was supported, in part, by a grant from the Office of Naval Research (N00014-03-1-0749) and the National Institutes of Health (GM065865). The United States government may have certain rights in the invention.

BACKGROUND OF THE INVENTION

Traditional approaches to reaction discovery typically focus on one particular chemical transformation. Predicted precursors for a target structure are chosen as substrates, and then particular reaction conditions are evaluated either manually or in a high-throughput format (Stambuli et al. Recent advances in the discovery of organometallic catalysts using high-throughput screening assays. *Curr. Opin. Chem. Biol.* 7, 420-426 (2003); Reetz, Combinatorial and evolution-based methods in the creation of enantioselective catalysts. *Angew. Chem. Int. Ed.* 40, 284-310 (2001); Stambuli et al. Screening of homogeneous catalysts by fluorescence resonance energy transfer. Identification of catalysts for room-temperature Heck reactions. *J. Am. Chem. Soc.* 123, 2677-8 (2001); Taylor et al. Thermographic selection of effective catalysts from an encoded polymer-bound library. *Science* 280, 267-70 (1998); Lober et al. Palladium-catalyzed hydroamination of 1,3-dienes: a colorimetric assay and enantioselective additions. *J. Am. Chem. Soc.* 123, 4366-7 (2001); Evans et al. Proton-activated fluorescence as a tool for simultaneous screening of combinatorial chemical reactions. *Curr. Opin. Chem. Biol.* 6, 333-338 (2002); each of which is incorporated herein by reference) for their ability to produce the desired target product. Although this approach is very useful in addressing specific chemical problems, it does not lend itself to the discovery of entirely new chemical reactions. In fact, its focused nature may leave many areas of chemical reactivity unexplored.

Recent developments in DNA-templated synthesis suggest that DNA annealing can organize many substrates in a single solution into DNA sequence-programmed pairs. DNA-templated synthesis and in vitro selection may, therefore, be used to evaluate many combinations of substrates and conditions for bond-forming reactions (Calderone et al. Directing otherwise incompatible reactions in a single solution by using DNA-templated organic synthesis. *Angew. Chem. Int. Ed.* 41, 4104-8 (2002); Gartner et al. The generality of DNA-templated synthesis as a basis for evolving non-natural small molecules. *J. Am. Chem. Soc.* 123, 6961-3 (2001); Gartner et al. Expanding the reaction scope of DNA-templated synthesis. *Angew. Chem. Int. Ed.* 41, 1796-1800 (2002); Rosenbaum et al. Efficient and Sequence-Specific DNA-Templated Polymerization of Peptide Nucleic Acid Aldehydes. *J. Am. Chem. Soc.* 125, 13924-5 (2003); each of which is incorporated herein by reference). See also published U.S. patent application 2004/018042, published Sep. 16, 2004, which is incorporated herein by reference. Watson-Crick base pairing controls the effective molarities of substrates tethered to DNA strands. Selection for bond formation, amplification by PCR, and DNA array analysis then reveals bond-forming substrate combinations and conditions. The versatility and efficiency of DNA-templated synthesis enables the discovery of reactions between substrates typically thought to be unreactive.

DNA-templated synthesis has now been used to discover new chemical reactions that are potentially broadly useful in the synthesis of chemical compounds such as pharmaceutical agents, new materials, polymers, catalysts, etc. In particular, a DNA-templated reaction discovery system has been used to discover a novel palladium-catalyzed carbon-carbon bond forming reaction. See U.S. patent application Ser. No. 11/205,493, filed Aug. 17, 2005; Kanan et al. "Reaction Discovery Enabled by DNA-Templated Synthesis and In Vitro Selection" *Nature* 431, 545-549 (2004); each of which is incorporated herein by reference. However, the need for DNA hybridization in the reaction discovery system limits the reaction conditions that can be explored. Duplex formation typically requires an aqueous solution with a relatively high salt concentration. Although water has been used extensively as a solvent for organic reactions (Li & Chan, *Organic Reactions in Aqueous Media* John Wiley & Sons, Inc., 1997; incorporated herein by reference), many ligands, catalysts, and reagents are insoluble in water. To access more traditional organic and organometallic chemistry reaction conditions in a selection-based approach to reaction discovery, alternative systems for organizing pairs of substrates in a single solution need to be explored.

SUMMARY OF THE INVENTION

Any reaction discovery system capable of simultaneously evaluating in a single solution many combinations of substrates for their ability to form new bonds and covalent structures should optimally address the following criteria: (1) the system should organize complex substrate mixtures into discrete pairs that can react (or not react) without affecting the reactivity of the other substrate pairs; (2) the system should include a general method for separating reactive substrate pairs from unreactive pairs; and (3) the reactive substrate pairs should be easily identifiable. Although DNA-templated reaction discovery satisfies each of these criteria, it is limited to exploring reaction conditions that facilitate DNA duplex formation (e.g., aqueous environments, lower temperatures, high salt concentrations).

The present invention stems from the recognition that many ligands, catalysts, and other reagents used by organic chemists are not soluble in the aqueous, high salt media needed for DNA duplex formation. Therefore, the instant reaction discovery system provides an alternative and improvement to previous reaction discovery systems based on DNA hybridization. The present system does not require duplex formation; instead, the potential substrate pairs are organized on a single nucleic acid (e.g., DNA) strand (i.e., the template). Since the inventive system does not require duplex formation, the reaction condition being explored may also include higher temperatures than possible with the earlier reaction discovery system.

To eliminate the need for duplex formation, a single pool of nucleic acid templates, each of which is linked to a unique pair of substrates is used in the inventive system. The two substrates are attached to the nucleic acid template molecule in such a way that they can react under suitable conditions. In certain embodiments, one substrate is attached to the 5'-end of the template via a cleavable linker. The other substrate is then attached proximal to the 5' end (e.g., at an internal modified base). The template molecule includes sequences encoding the identity of each of the substrates attached thereto. Thus, as shown in FIG. 1, each unique pair of substrates to be tested is linked to a unique template that encodes the identity of the two substrates. Substrates attached in this manner to single nucleic acid template molecule have the same opportunity to react with each other under suitable reaction conditions, similar to substrates attached to two different DNA strands in a DNA duplex.

Although the invention reaction discovery system does not require nucleic acid hybridization, the solubility of the nucleic acid template molecule is addressed. In certain embodiments, the reaction discovery method is performed at low concentrations (e.g., 0.1-0.0001 μM) to facilitate the solubility of the template molecules. In other embodiments, an organic solvent-water mixture is used as the solvent. In many cases, ligands, catalysts, and other reagents are insoluble in 100% aqueous solutions but are readily soluble in organic solvent-water mixtures (e.g., mixed aqueous-organic systems that include miscible organic solvents such as acetonitrile, DMF, DMSO, methanol, or dioxane). Furthermore, in certain embodiments, solubility of the template molecule may be enhanced by the use of ammonium salts such as tetraalkylammonium salts.

In one aspect, pools of template molecules with pairs of substrates attached are dissolved in an organic solvent or an organic solvent-water mixture. See, e.g., FIG. 2. The solution is then subjected to a particular reaction condition (e.g., temperature, catalyst, reagent, etc.). The pool of template molecules is then exposed to conditions that cleave one of the substrates from the template molecule (e.g., a reducing agent to cleave a disulfide bond). If the substrate did not form a direct covalent bond with the other substrate attached to the template molecule, it will be completely free of the template molecule. If the substrate did form a covalent bond under the reaction conditions the pool was subjected to, it will remain attached to the template molecule through the other substrate. In certain embodiments, the cleavable substrate also is attached to biotin; therefore, substrate combinations that have reacted to form a covalent bond remain covalently linked to biotin and can be isolated using a streptavidin resin or streptavidin-linked magnetic particles. The template molecule with substrate combinations that did not form a covalent bond are not linked to biotin after the cleavage reaction and are therefore washed away. The sequences of the isolated substrate combinations that reacted to form a covalent bond are then optionally amplified (e.g., using PCR) and analyzed to identify the identities of the reacting substrates. Traditional DNA sequence may be used to analyze the results, or DNA microarray technology may be used (see, e.g., FIGS. 15-22). As will be appreciated by one of skill in this art, multiple selections and analyses may be performed in parallel. Therefore, many different reaction conditions may be screened at once. DNA microarray technologies are particularly useful in analyzing matrices of substrates. The present invention also includes any novel chemical reactions that are discovered using the inventive method and system of discovering new chemical reactions.

In another aspect, the invention provides a system for preparing the template molecules with the substrate combinations attached. The inventive reaction discovery system utilizes nucleic acid template molecules attached to two substrates. A modular approach has been developed for preparing a pool of substrate combinations attached to a nucleic acid template molecule. The system typically involves attaching single substrates to an oligonucleotide and then using enzymatic steps to assemble the full-length template as shown in FIGS. 4 and 14. For example, in the first step, primer extension from an overhang adds a sequence encoding one substrate to the 3' end of a sequence encoding another substrate that is already attached to the oligonucleotide at an internal modified base. The resulting template molecule contains one primer binding site and coding regions for both substrates. This template molecule is attached to one substrate of the pair. In the second step, ligation appends an oligonucleotide with a substrate attached to its 5' end via a cleavable biotinylated linker to the 5' end of the template from the first step. The template molecules are prepared individually or are prepared in parallel (e.g., 5-100 or more at a time). In certain embodiments, the resulting full-length template molecule contains two primer binding sites, two coding regions, and the substrate pair to be tested in various reaction conditions. In this way, one substrate is attached at the 5' end, and the other substrate is attached at an internal modified base (e.g., dT). In another embodiments, the system involves labeling an oligonucleotide with two substrates. This addition of substrates to an oligonucleotide are performed using techniques for modifying oligonucleotides known in the art. The template molecules with the substrates attached and any intermediates thereto are also considered to be within the scope of the invention. In certain embodiments, the inventive template molecule is DNA-based and includes two substrates covalently attached thereto and sequences identifying the attached substrates. The template molecule optionally also includes primer sequences for PCR amplification and/or sequencing.

The present invention also provides kits for practicing the inventive reaction discovery technology. These kits may include possible substrates, template molecules, DNA molecules, nucleotides, nucleotide analogs, primers, buffers, enzymes (e.g., polymerases, ligases, etc.), catalysts, reagents, ligands, organic solvents, microarrays, reagents for polyacrylamide gel electrophoresis, columns, resins, affinity reagents, or other materials that would be useful in practicing the present invention. Preferably, the materials are conveniently packaged with instructions for use. The kits may provide enough materials for any number of rounds of screening for new reactions. In certain embodiments, the kit is designed to allow the user to substitute in his or her own substrates, catalysts, solvent systems, or other reagents. In certain particular embodiments, the kit is designed to allow the user to test his or her own reactions conditions.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books (Sausalito, Calif.), 1999; and Kemp and Vellaccio, *Organic Chemistry*, Worth Publishers, Inc. (New York), 1980; the entire contents of which are incorporated herein by reference.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$(CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2$ $R_x$; —$NR_x$(CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$(CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term, associated with, is used to describe the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be through an amide, ester, carbon-carbon, disulfide, carbamate, ether, or carbonate linkage. The covalent association may also include a linker moiety such as a cleavable linker (e.g., disulfide linker, photocleavable linker, etc.). Desirable non-covalent interactions include hydrogen bonding, van der Waals interactions, hydrophobic interactions, magnetic interactions, electrostatic interactions, etc.

Polynucleotide, nucleic acid, or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A protein comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. A protein may refer to a full-length protein or a fragment of a protein. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term small molecule, as used herein, refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it possesses one or more of the following characteristics including having several carbon-carbon bonds, having multiple stereocenters, having multiple functional groups, having at least two different types of functional groups, and having a molecular weight of less than 1500, although this characterization is not intended to be limiting for the purposes of the present invention.

BRIEF DESCRIPTION OF THE DRAWING

FIG. 10 shows B-oligos: generalized (SEQ ID NO: 3) and labeled with pool B substrates B1-B14 (SEQ ID NOs: 4-17).

FIG. 11 shows B-oligos: generalized (SEQ ID NO: 18) and labeled with pool A substrates A1-A14 (SEQ ID NO: 19).

FIG. 12 shows A-oligos labeled with pool A substrates.

FIG. 13 shows A-oligos labeled with pool B substrates.

FIG. 20 demonstrates the use of the reaction discovery system to screen for bond forming reaction mediated by Pd(II). Reaction conditions included 1 mM Pd(II) in MOPS buffer pH 7 for 20 minutes at four different temperatures: 25° C., 37° C., 50° C., and 65° C.

DETAILED DESCRIPTION OF CERTAIN PREFERRED EMBODIMENTS OF THE INVENTION

Figure 1:
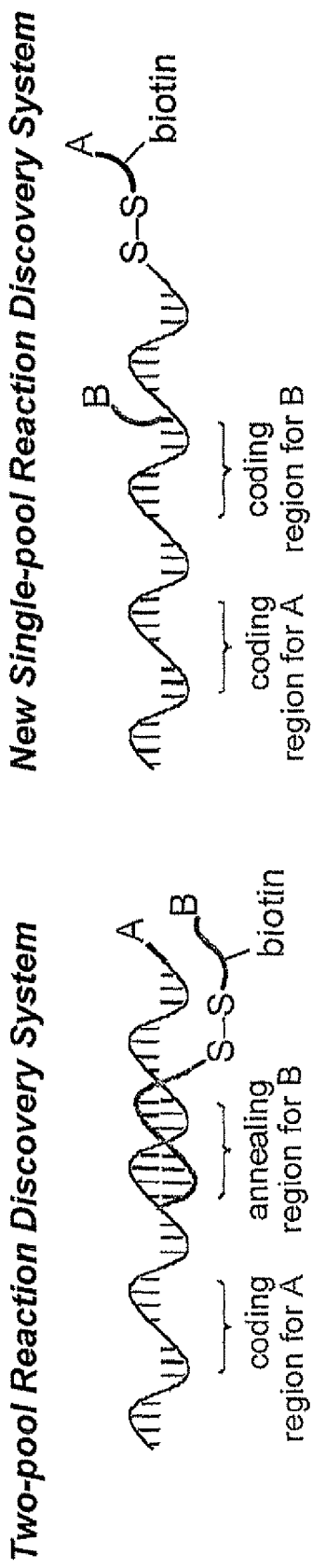
FIG. 1 is a comparison of the substrate organization used in a two-pool reaction discovery system versus a single-pool reaction discovery system.

The present invention provides a system for discovering new chemical reactions. This novel system for discovering new chemical reactivity and reactions is not encumbered by conventional wisdom with regard to functional group reactivity and allows for the examination of a broad range of both reaction conditions and substrates in a highly efficient manner. The inventive method of discovering new chemical reactions and chemical reactivity has several advantages over existing methods. For example, several groups have developed high-throughput screens to test the efficiency of a particular reaction under a variety of conditions (Kuntz et al. *Current Opinion in Chemical Biology* 3:313-319, 1999; Francis et al. *Curr. Opin. Chem. Biol.* 2:422-428, 1998; Pawlas et al. *J. Am. Chem. Soc.* 124:3669-3679, 2002; Lober et al. *J. Am. Chem. Soc.* 123:4366-4367, 2001; Evans et al. *Curr. Opin. Chem. Biol.* 6:333-338, 2002; Taylor et al. *Science* 280:267-270, 1998; Stambuli et al. *J. Am. Chem. Soc.* 123: 2677-2678, 2001; each of which is incorporated herein by reference); however, these screens are limited to a small set of reaction types. Reactions have been analyzed in a high-throughput manner using fluorescence spectroscopy, colorimetric assay, thermographic analysis, and traditional chromatography (Dahmen et al. *Synthesis-Stuttgart* 1431-1449, 2001; Wennemers *Combinatorial Chemistry & High Throughput Screening* 4:273-285, 2001; each of which is incorporated herein by reference). Most high-throughput screens for chemical reactivity are useful for only a small set of reaction types because the screen depends on a particular property of the reaction such as the disappearance of an amine or the production of protons. As a result, high throughput screening methods can be useful for discovering catalysts for a known or anticipated reason, but are poorly suited to discover novel reactivity different from a reaction of interest.

A non-biased search for chemical reactions would examine a broad range of both reaction conditions and substrates in a highly efficient manner that is practical on the scale of thousands of different reactions. In certain embodiments, the inventive system only requires nanomolar, picomolar, or femtomolar quantities of material per reaction discovery experiment. The inventive system for discovering novel chemical reactions offers a much greater chance of discovering unexpected and unprecedented reactivity that may lead to new insights into reactivity and to useful new reactions for chemical synthesis.

The inventive system also differs from a previously disclosed reaction discovery system (see U.S. patent application, U.S. Ser. No. 60/404,395, filed Aug. 19, 2002; U.S. Ser. No. 10/643,752, filed Aug. 19, 2003; U.S. Ser. No. 60/602,255, filed Aug. 17, 2004; and U.S. Ser. No. 11/205,492, filed Aug. 17, 2005; each of which is incorporated herein by reference) in that the instant system does not rely on nucleic acid hybridization to bring the two potential substrates together. Hybridization unfortunately limits the reaction conditions that can be explored using the previous system because duplex formation typically requires an aqueous solution with a relatively high salt concentration at a relatively low temperature.

Non-DNA Templated Reaction Discovery

The new system allows for a broader, non-biased search for chemical reactivity of a large number of diverse reactants in parallel. Although some chemical reactions are compatible with water as the solvent, the vast majority of ligands, catalysts, and reagents that are used by organic chemists are not compatible with an aqueous solvent and/or are not soluble in aqueous solutions. To access these reaction conditions, a new selection-based approach to reaction discovery was developed in which organic solvents or organic solvent/water mixtures can be used as solvent and higher temperature can be utilized. In addition, the new system requires less material per reaction discovery experiment than the DNA-templated approach. The new system, therefore, allows for a broader exploration of reactivity space than any previous systems for reaction discovery.

This new approach involves attaching substrate pairs on the same nucleic acid strand. The substrates are attached to the strand in such a manner that they are able to react with each other under suitable conditions and successful reaction of the substrate pair allows for selection and identification of the substrates. The reactivity of these substrates under many different conditions (e.g., solvent, catalysts, pH, reagents, etc.) may be evaluated. The sequence of the template molecule is used to identify the substrates attached to the template. The present invention also includes any new chemical reactions that are discovered using the inventive method and system of discovering new chemical reactions.

The inventive system first involves preparing a template with a substrate pair attached. The template is then subjected to test reaction conditions, and the template is subsequently selected if the reaction conditions have effected a direct covalent attachment between the two substrates on the template. The sequence of the template is then optionally determined to identify the successfully reacting substrates. In certain embodiments, DNA microarray technology is used to identify the reacted substrate pairs. The system is particularly amenable for analyzing many different combinations of substrates and reaction conditions in parallel. The system also allows for the testing of a library of different template molecules to be performed in one pot.

Figure 2:
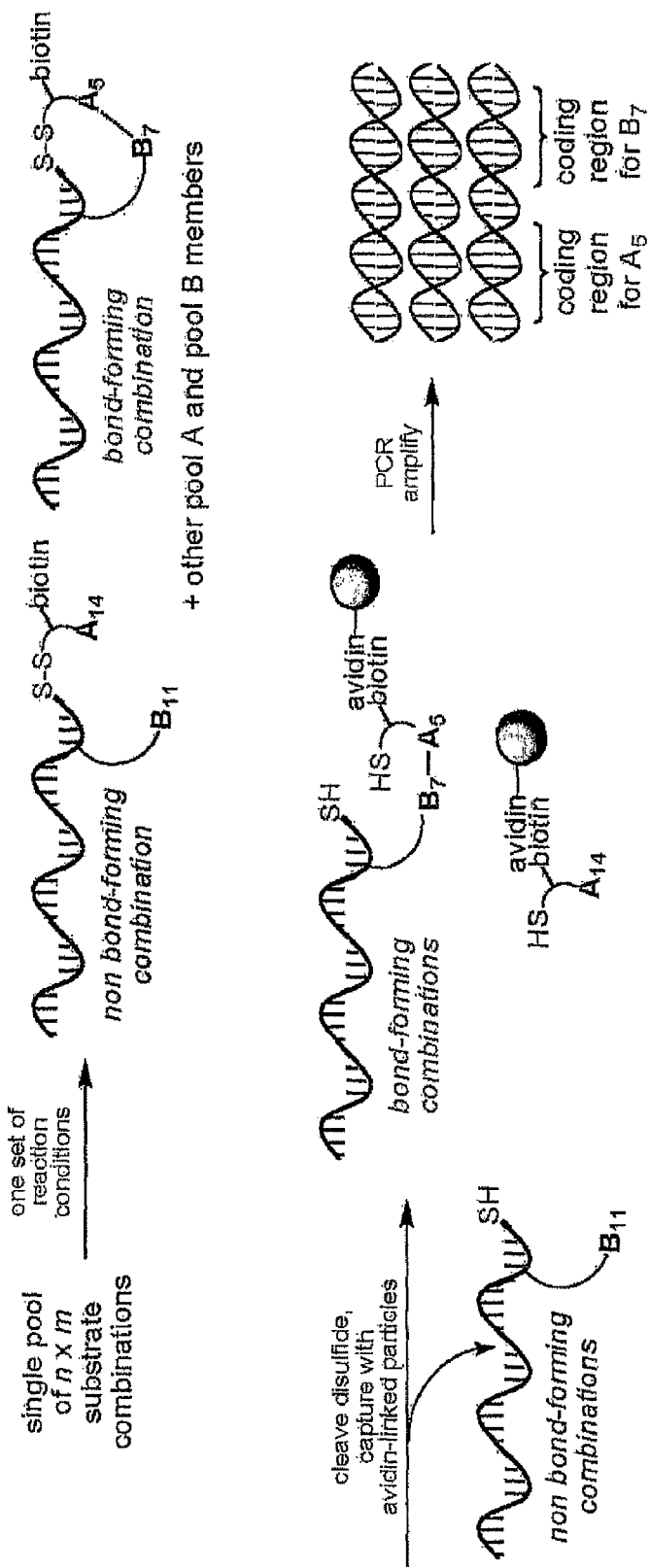
FIG. 2 shows a selection for bond forming reaction in the inventive single-pool reaction discovery system.
Figure 3:
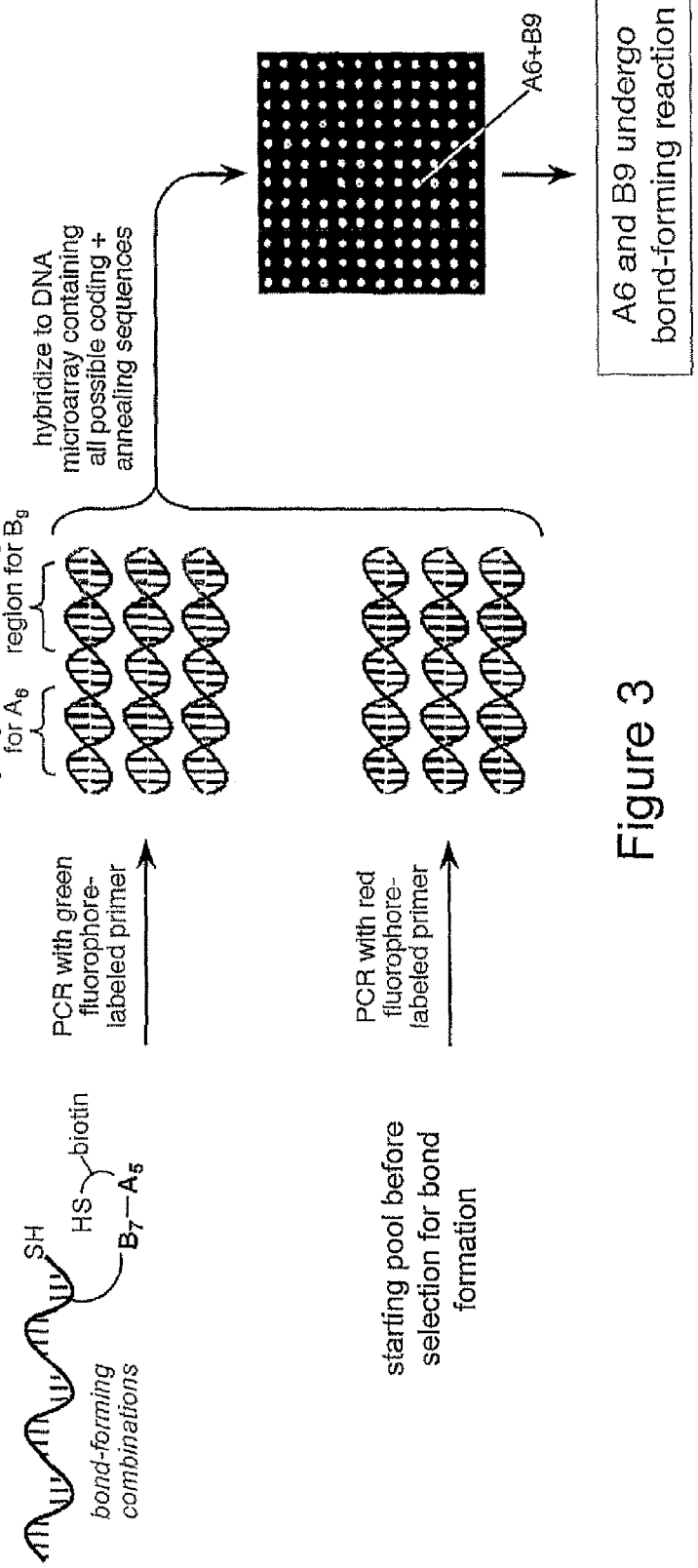
FIG. 3 shows the analysis of polynucleotide sequences encoding bond-forming reactions.

The template typically includes two substrates and sequences that identify the attached substrates. The template may be any nucleic acid molecule. In certain embodiments, the template is DNA. In other embodiments, the template is RNA. In other embodiments, the template is a derivative of DNA or RNA. For example, the template may include unnatural bases. In certain embodiments, an unnatural bases is used to attach one of the substrates to the template. The two substrates may be attached anywhere along the template molecule. The substrates are typically attached in such a manner that they will react under suitable conditions. In certain embodiments, at least one substrate is attached at an end of the template. In other embodiments, at least one substrate it attached to an internal base of the template. For example, one of the substrates may be attached to a modified base such as amino-modified deoxythymidine. In certain particular embodiments, one substrate is attached to an end of the template, and the other substrate is attached to an internal base of the template. In other embodiments, both substrates are attached to an internal base of the template. In still other embodiments, both substrates are attached to the same or opposite ends of the template. The two substrates are usually attached at less than 100, 75, 50, 40, 30, 25, 20, 15, 10, or 5 bases from each other. In certain particular embodiments, the two substrates are attached at a distance between 1 and 20 bases from each other. In certain particular embodiments, the two substrates are attached at a distance between 5 and 15 bases from each other. In certain embodiments, the substrate is attached to the template through a linker. In certain embodiments, the linker contains 1-20 carbons or heteroatoms. In certain particular embodiments, the linker contains 1-10 carbons or heteroatoms. In certain embodiments, the linker contains approximately 6 carbon atoms or heteroatoms. In certain embodiments, the linker is substituted. In other embodiments, the linker is unsubstituted. In certain embodiments, the linker include cyclic structures. In other embodiments, the linker does not include cyclic structures. In certain embodiments, the linker is cleavable. Exemplary cleavable linkers include disulfide bonds, ester bonds, amide bonds, etc. In certain embodiments, a disulfide bond is used to link the substrate to the end of the template. The linker may also include an affinity agent such as biotin. Other affinity agents useful in the present invention include polyhistidine, antibody, fragments of antibodies, epitopes, etc. In certain embodiments, when the linker is cleaved the substrate attached through the linker to the template and the affinity agent are released from the template as shown in FIGS. 2-3.

The substrates attached to the template may include any chemical functional group. Particularly interesting are reactive functional groups that have been shown to be useful in other chemical reactions. Functional groups that have shown to be useful in carbon-carbon bond forming reactions are particularly useful. Exemplary substrates include aliphatic halides (e.g., alkyl halides, akenyl halides, akynyl halides), aryl halides, esters, amides, carbonates, carbamates, ureas, alcohols, thiols, amines (e.g., aliphatic amines, aryl amines, dialiphatic amines, trialiphatic amines, etc.), alkyls, alkenes, alkynes, aryls, heteroaryls, phosphorus-containing groups (e.g., phosphonium salts), etc.

The template molecule typically contains sequence that encode the identity of the substrates attached to the template (i.e., encoding sequences). Depending on the number of substrates, the identity of the attached substrates is encoded in 2, 3, 4, 5, 6, 7, 8, 9, 10, or more bases. Each substrate used in a library is associated with its own identifying sequences. The template also may contain other sequences useful in the present invention. For example, the template may include primer sequences. In certain embodiments, the primer sequences are useful for amplifying the template nucleic acid by the PCR. In other embodiments, the primer sequences are useful for determining the sequence of the template. The template may also contain linking sequences that link the various encoding sequences or primer sequences together.

Once the template is prepared with its substrate combination, it is exposed to a particular set of reaction conditions. In certain embodiments, the template is exposed to one set of reaction conditions. The template may also be exposed to a sequence of multiple reaction conditions. The reaction conditions may include solvent, pH, catalyst, ligand, salt concentration, stoichiometric reagent, activating reagent, deprotecting reagent, protecting reagent, temperature, pressure, duration of reaction, presence of water, presence of oxygen, presence of another gas, presence of a metal, presence of a surface, presence of an ion, etc. In certain embodiments, the reaction conditions include an organometallic catalyst (e.g., Pd, Pt, Co, Mo, Cu, Zn, Os, Hg, etc.). In certain particular embodiments, the reaction conditions include a catalyst that has been shown to be useful in carbon-carbon bond forming reactions. In other embodiments, the reaction conditions include the addition of an acid or base. In certain embodiments, the reaction conditions include an acidic pH (<7). In other embodiments, the reaction conditions include a basic pH (>7). In still other embodiments, the reaction conditions include a neutral pH (approximately 7). In certain embodiments, the reaction conditions include a chiral reagent.

In certain embodiments, the reaction conditions include an organic solvent. Exemplary organic solvent useful in the present invention include acetonitrile, tetrahydrofuran (THF), chloroform, methylene chloride, dimethylformamide (DMF), DMSO, dioxane, benzene, toluene, diethyl ether, hexanes, ethanol, methanol, etc. The solvent used may also include a mixture of an organic solvent and water. In certain embodiments, the reaction conditions include a mixed aqueous-organic solvent including acetonitrile, DMF, DMSO, methanol, or dixoane. The percentage of water in the mixture may range from 0% to 50%. In certain embodiments, the percentage of water in the mixture is approximately 1%, 2%, 3%, 4%, 5%, 10%, 15%, 20%, 25%, 30%, 40%, or 50%. In certain embodiments, the reaction mixture include no water or at least as little water as is reasonable possible. In other embodiments, the reaction conditions include an aqueous system. In certain particular embodiments, the aqueous system is buffered at a particular pH.

In certain embodiments, the reactions conditions include a particular temperature. The inventive system is particular useful to explore reaction condition at higher than ambient temperature because the inventive system does not require duplex formation. In certain embodiments, temperature ranges from −78° C. to 200° C. In other embodiments, the temperature ranges from 0° C. to 200° C. In yet other embodiments, the temperature ranges from 25° C. to 200° C. In yet other embodiments, the temperature ranges from 30° C. to 200° C. In yet other embodiments, the temperature ranges from 20° C. to 100° C. In yet other embodiments, the temperature ranges from 25° C. to 100° C. In yet other embodiments, the temperature ranges from 30° C. to 100° C. In certain embodiments, the temperature of the reaction conditions is approximately 10° C., 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., or 200° C. In certain embodiments, the temperature of the reaction conditions is approximately 25° C. In certain embodiments, the temperature of the reaction conditions is approximately 37° C. In certain embodiments, the temperature of the reaction conditions is approximately 50° C. In certain embodiments, the temperature of the reaction conditions is approximately 65° C. In certain embodiments, the temperature of the reaction conditions is approximately 95° C. In certain embodiments, the temperature of the reaction conditions is less than 100° C.

After the template has been exposed to the desired test reaction conditions, the cleavable linker is cleaved using an appropriate reagent. If the reaction conditions have not resulted in the formation of a direct covalent linkage between the two substrates, cleavage of the linker will result in one of the substrates and the affinity reagent being completely removed from the template. In the case of a disulfide linkage being used, any reducing reagent may be used to cleave the linkage. In certain embodiments, high concentrations of tris-(2-carboxyethyl)phosphine hydrochloride are used to cleave the disulfide linker. For an ester or amide linker, an esterase or amidase may be used to cleave the linker, respectively. In the case of an amide linker, a protease may also be used to cleave the linker. Such ester and amide linkers may also be cleaved by acid or base hydrolysis. The chemistry used to cleave the linker should not modify or cleave any covalent bond that may have formed between the two substrates. Those templates that include substrate combinations that have reacted to form a covalent bond will remain covalently linked to the affinity reagent through one of the substrates (e.g., attached through the internal modified base). The templates with substrate combinations that have reacted can then be isolated using a resin known to bind the affinity reagent. For example, with a biotin affinity reagent, streptavidin beads can be used to isolate the templates with substrate combinations that have reacted to form a covalent bond.

Once the templates with substrate combinations that have reacted are isolated, the attached nucleic acid sequence may be analyzed to determine the identity of the substrates. In certain embodiments, the template nucleic acid is first amplified by the PCR. The sequence of the nucleic acid is then determined by traditional sequencing of the nucleic acid, by micro-array based methods, by mass spectral analysis, or by any other methods used to determine the sequence of a nucleic acid. The PCR amplification allows a researcher to perform selection on pmol quantities of material so that even a single nmol-scale preparation of the original template can provide enough material for the testing of thousands of different reactions conditions.

In other embodiments, microarray technology is used to identify the substrate pairs that results in bond formation under the test reaction conditions. The analysis using microarray technology is illustrated in FIG. 15-22. DNA microarray are printed with oligonucleotide probes that correspond to each encoding oligonucleotide in a library. For example, the probes may correspond to each permutation of substrates including homocoupling. In certain embodiments, the microarray also includes standards. In certain embodiments, the array includes positive controls that correspond to known reaction. In certain embodiments, the array includes negative controls that correspond to substrates that are known not to react under the test reaction conditions. The selected oligonucleotides with substrate pairs that have reacted are then allowed to hybridize to the array, and spots with hybridized probe indicate that a reaction took place between the substrates under the test reaction conditions.

The inventive reaction discovery system combines in vitro selection with the use of nucleic acid technology to efficiently search for novel bond-forming reaction independent of reactant structures. The ability to select directly for covalent bond formation, the minute scale required for analysis (e.g., 1 pmol total material of template molecules per discovery experiment), and compatibility of the system with a wide variety of reaction conditions enables the search for unprecedented reactivity that can examine thousands of combinations of reactants and reaction conditions in one or several experiments as shown in FIGS. 17-22.

Figure 7:
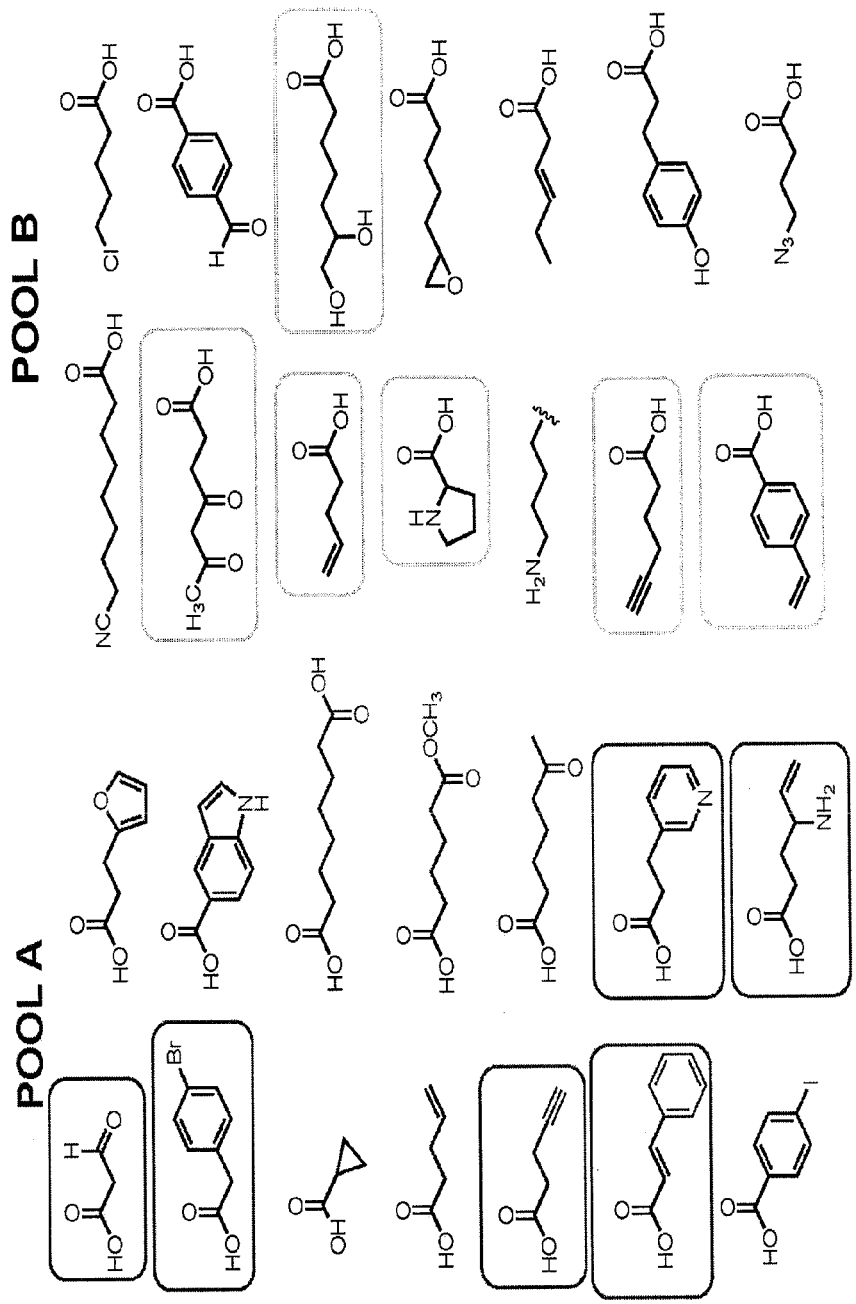
FIG. 7 shows exemplary substrate structures.
Figure 8:
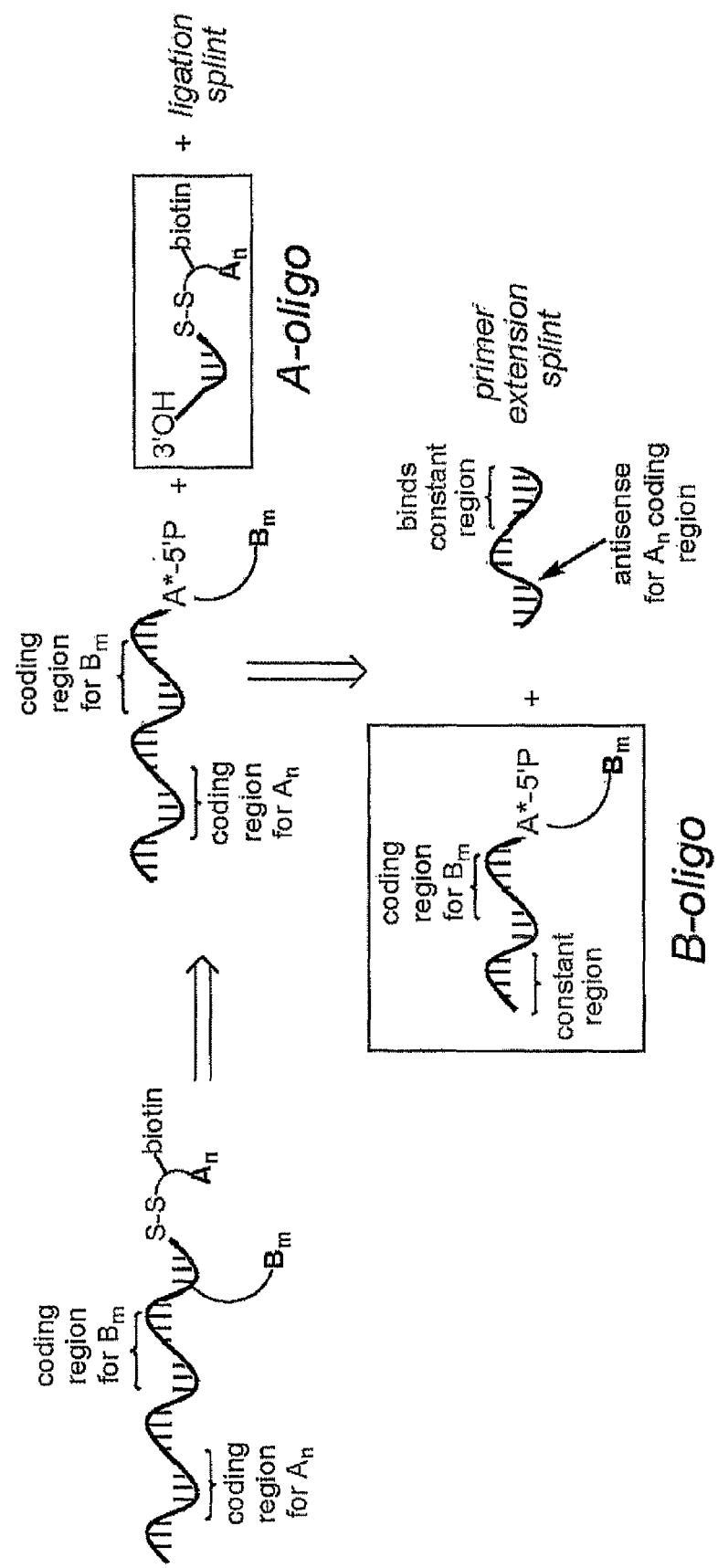
FIG. 8 shows details of a matrix assembly strategy.
Figure 9:
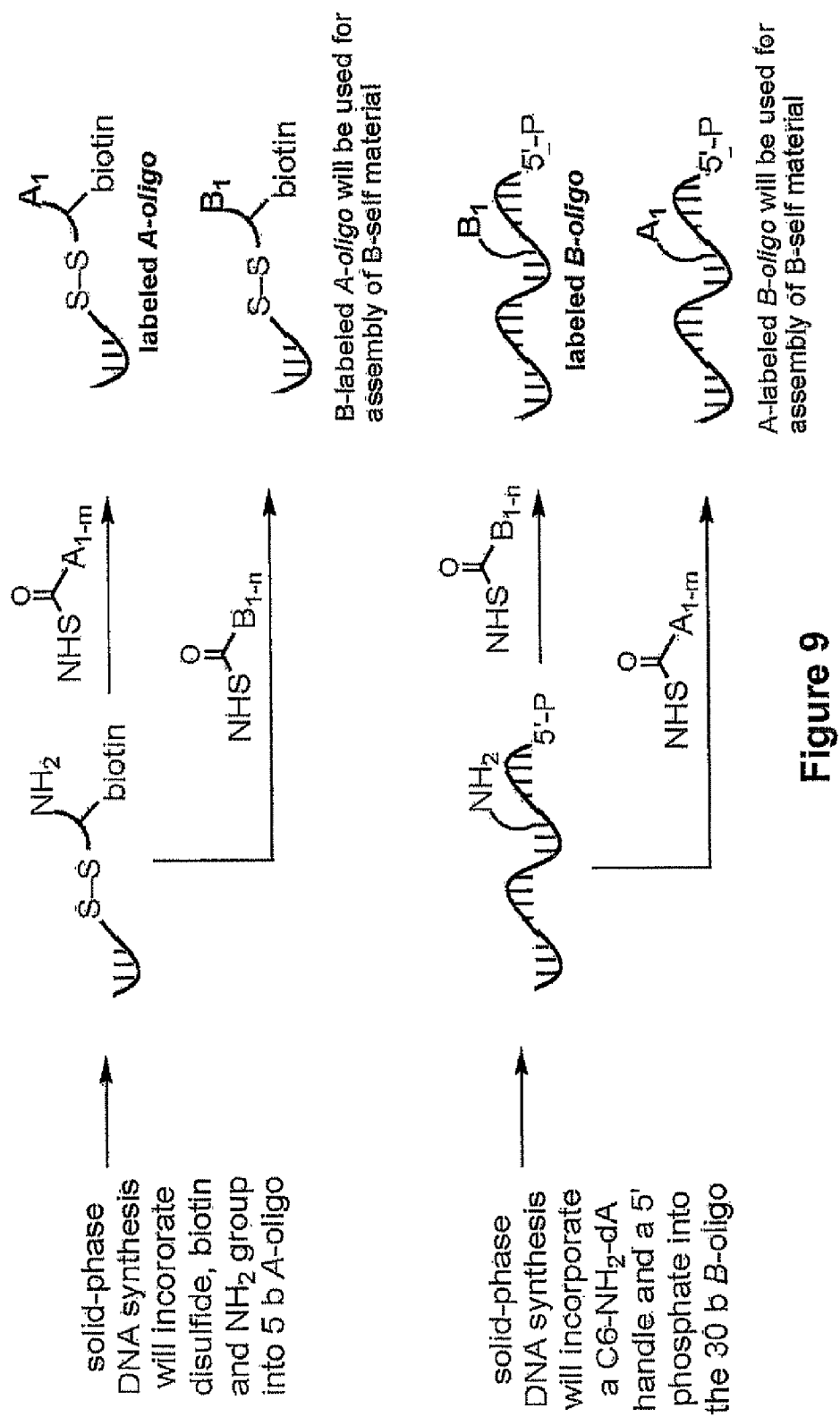
FIG. 9 shows component preparation for matrix assembly.
Figure 14:
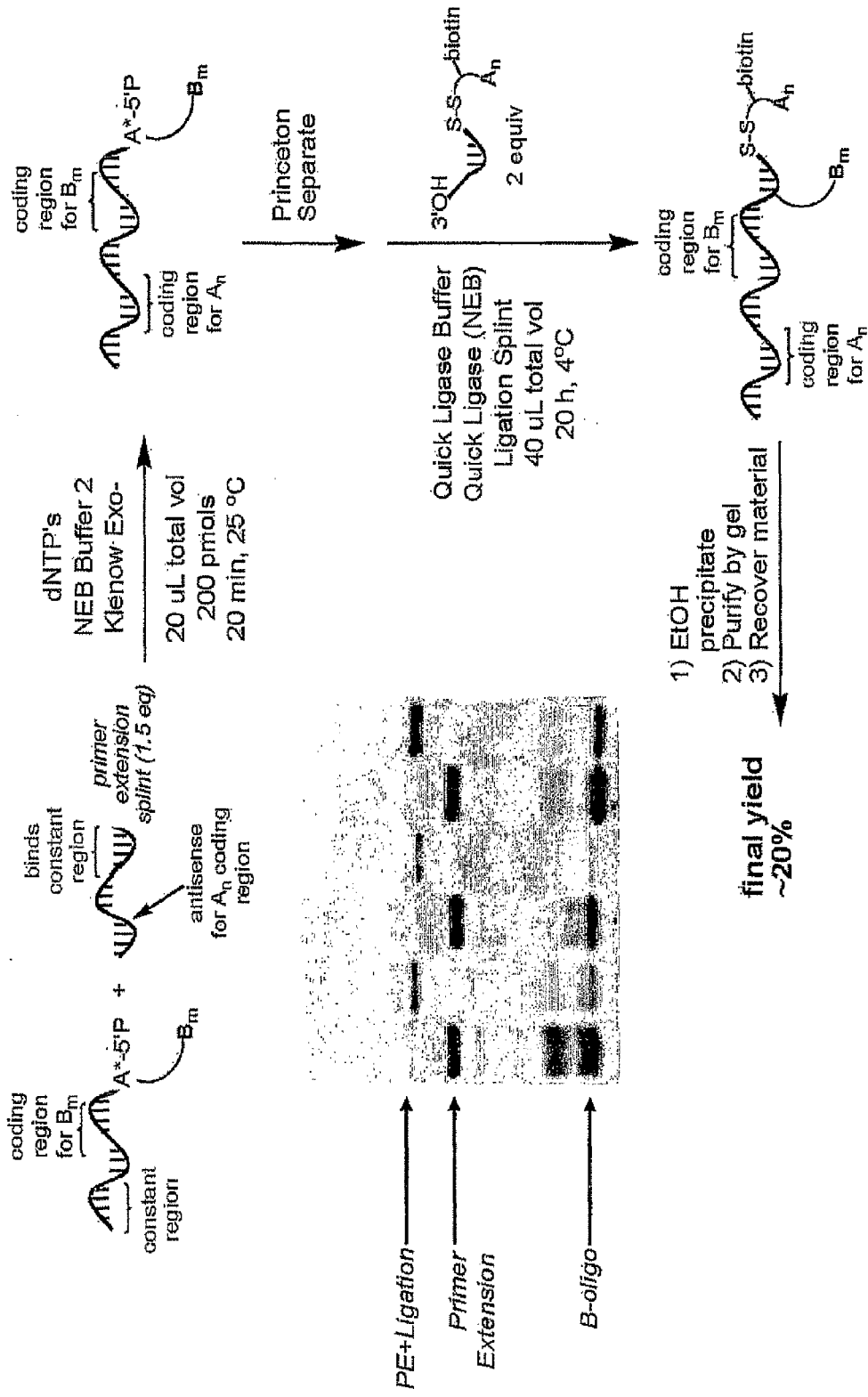
FIG. 14 shows an exemplary assembly of templates with two substrates attached useful in the inventive reaction discovery system. The assembly includes adding the $A_n$ coding region onto an oligonucleotide with the substrate $B_m$ attached using a primer extension reaction. The substrate $A_n$ with its biotin disulfide linker is then ligated onto the 5' end to form the full template.
Figure 15:
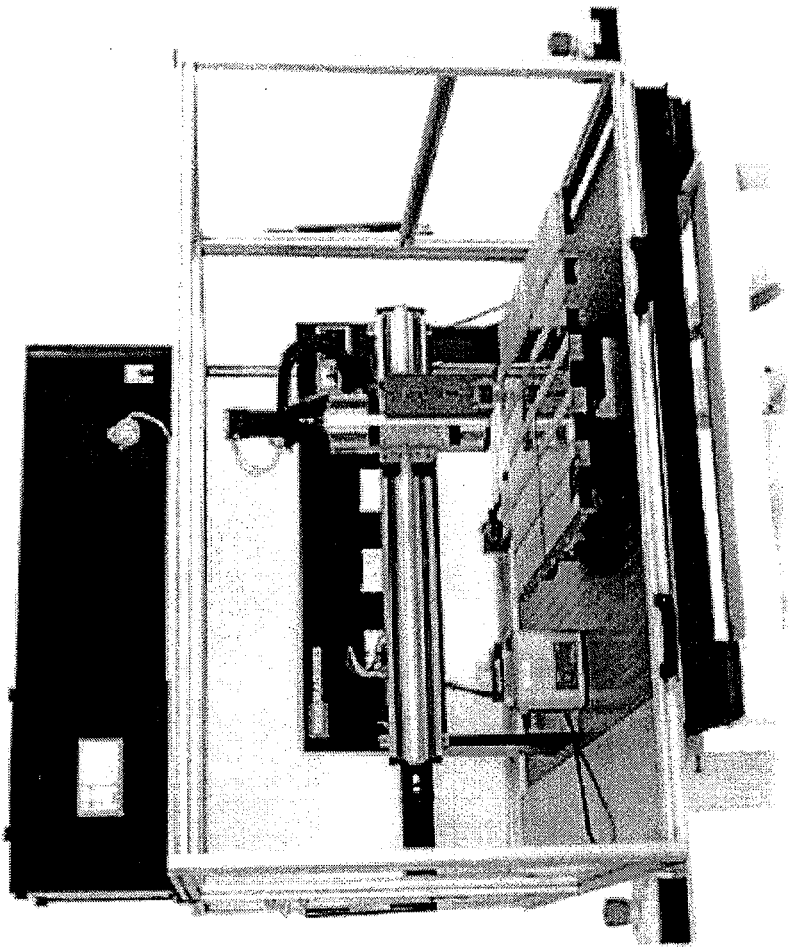
FIG. 15 demonstrates the use of microarray technology to analyze the results of the bonding forming reaction conditions. Each spot on the DNA microarray corresponds to an $A_m \times B_n$ encoding oligo template. Arrays were printed using a Genemachines OmniGrid instrument in the Bauer Center for Genomics Research at Harvard University.
Figure 16:
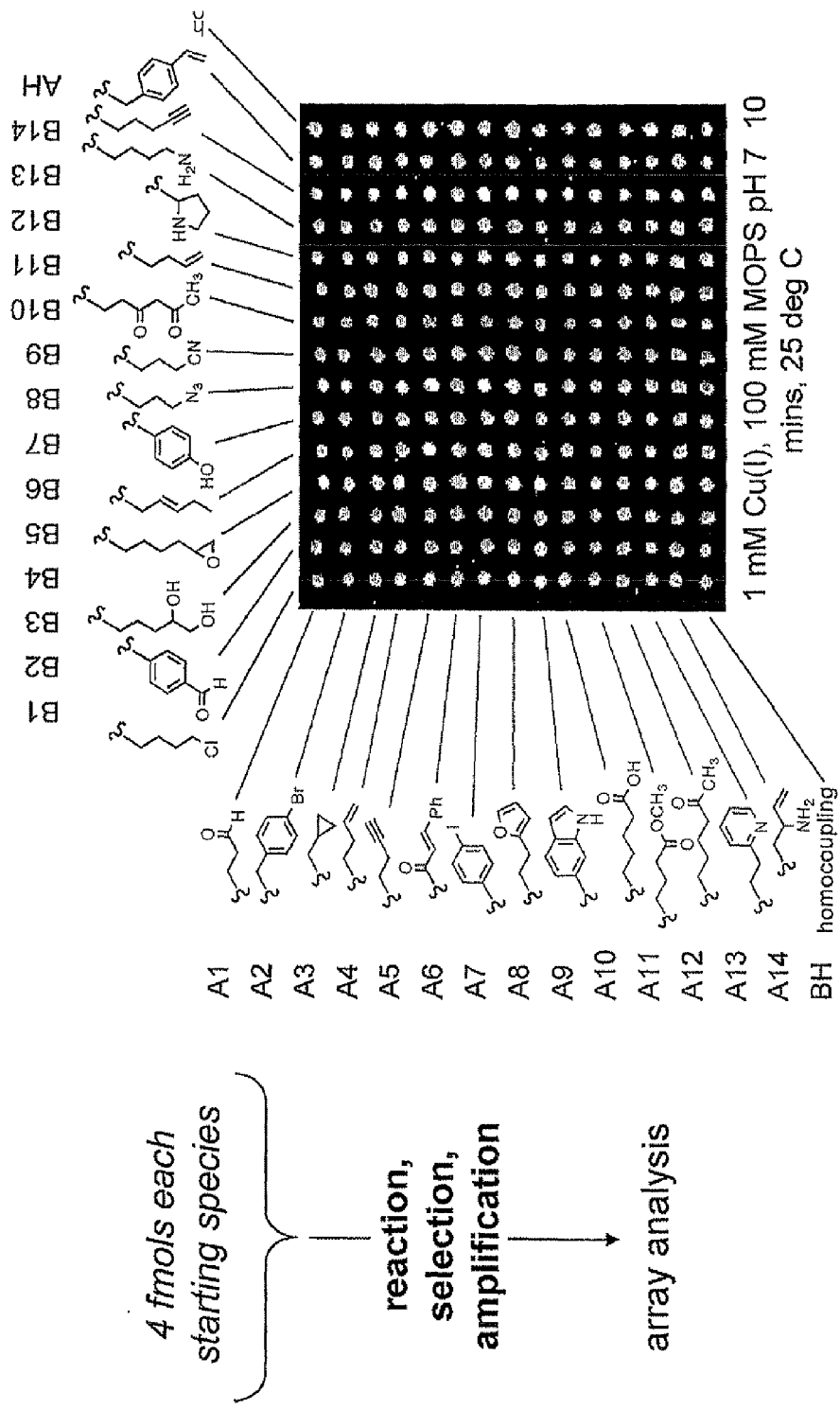
FIG. 16 shows a microarray analysis used to validate the inventive reaction discovery system by screening for known bond forming reactions.
Figure 17:
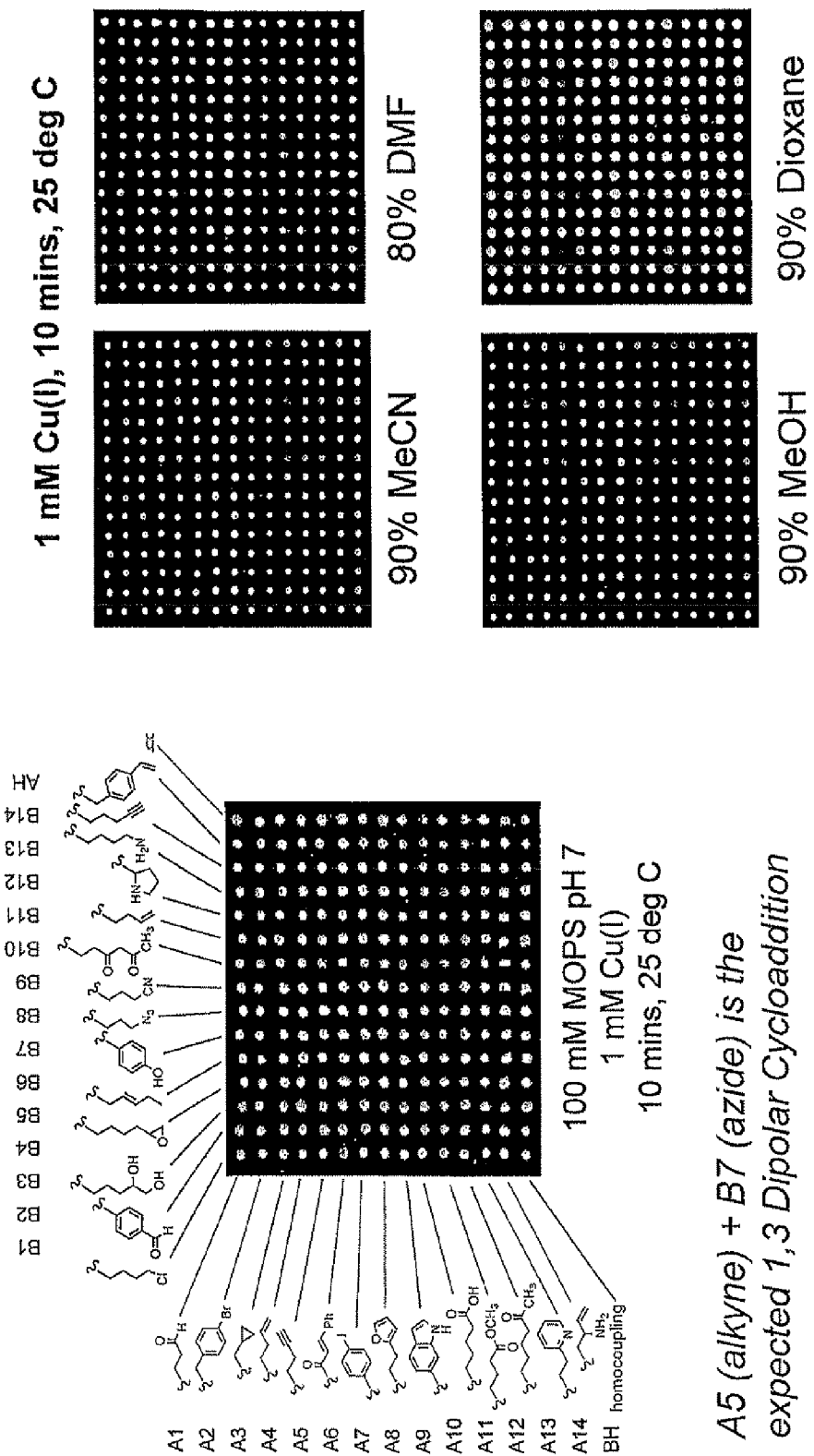
FIG. 17 demonstrates the use of the reaction discovery system to screen for bond forming reaction mediated by Cu(I). Reaction conditions included 1 mM Cu(I) for 10 minutes at 25° C. in four different aqueous solvent mixtures: 90% acetonitrile ($CH_3CN$), 80% DMF, 90% methanol, and 90% dioxane.
Figure 18:
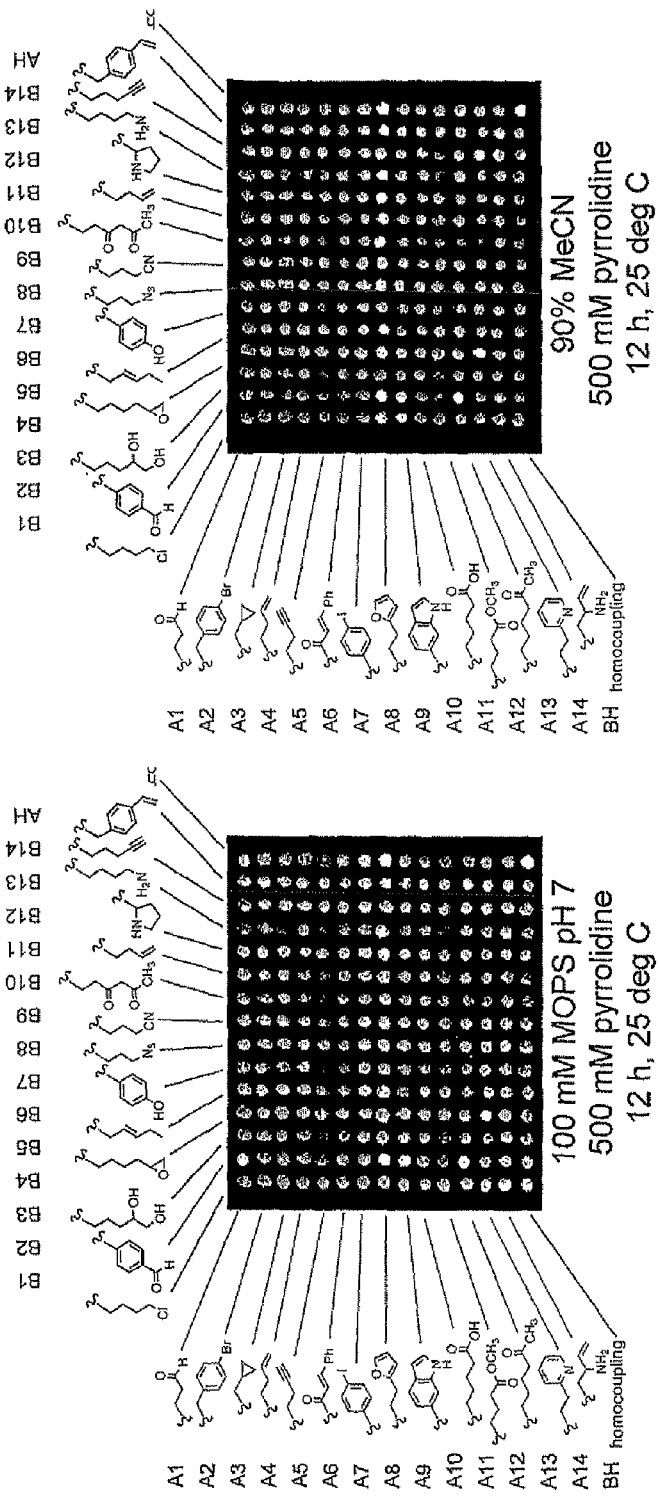
FIG. 18 demonstrates further use of the inventive reaction discovery system to explore enamine chemistry. The pyrrolidine in the reactions is expected to mediate an enamine aldol reaction (e.g., between ketone (A12) and aryl aldehyde (B2).
Figure 19:
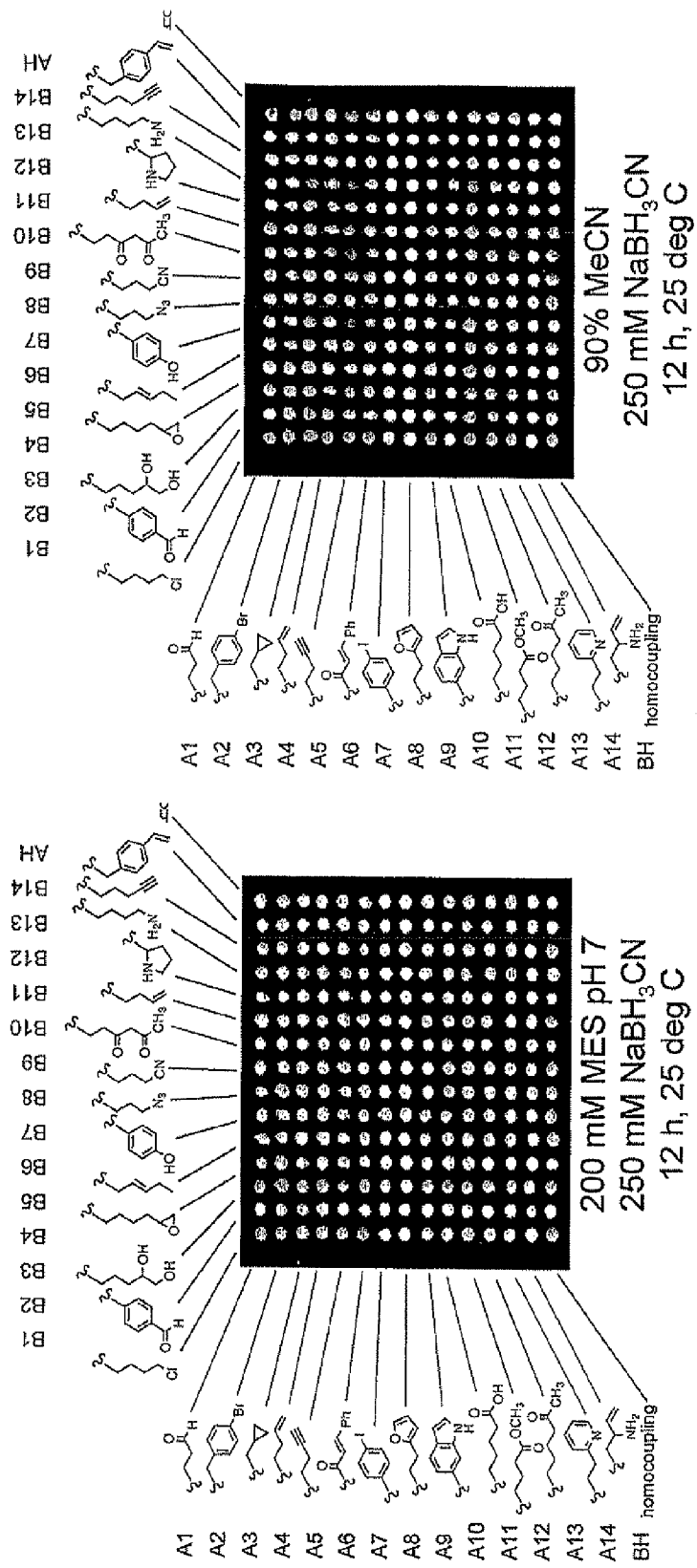
FIG. 19 demonstrates further use of the inventive reaction discovery system to explore reductive amination chemistry.

In certain embodiments, a library of template molecules with various combinations of substrates are prepared. See, for example, FIG. 7. In certain embodiments, all possible combinations of a set of substrates are provided for in a library of template molecules. The library of templates may contain at least 10 members, 20 members, 30 members, 50 members, 100 members, 250 members, 500 members, or 1,000 members. In certain embodiments, all the members of a library are combined in one pot and subjected to a specific set of reaction conditions. In certain embodiments, 0.1-100 pmol of total material of library templates are used in a round of reaction discovery. In certain embodiments, 1-50 pmol of material are used. In other embodiments, 1-10 pmol are used. In yet other embodiments, approximately 1 pmol of material is used in a reaction discovery experiment. Each of the members of the library may be subjected to tens, hundreds, or thousands of different reaction conditions.

Preparation of Template Molecules

The present invention also provides methods of preparing the templates useful in the present reaction discovery system. Any method may be used to prepare the templates with the pair of substrates, the linker, affinity reagent, and identifying sequences. Techniques are known in the art for preparing DNA molecules of any sequence and modifying those sequences (Ausubel et al., eds., *Current Protocols in Molecular Biology*, 1987; Sambrook et al. *Molecular Cloning: A Laboratory Manual*, 2nd Ed., 1989; each of which is incorporated herein by reference). For example, the DNA molecule may be prepared by a DNA synthesizer and subsequently modified at the termini or at an internal base. In certain embodiments, a modified internal base is inserted into the sequence to be later modified by attaching a substrate. In certain embodiments, two modified internal bases, which are later modified by attaching a substrate, are inserted into the sequence at a pre-determined distance apart (e.g., 1-15 bases apart).

Figure 4:
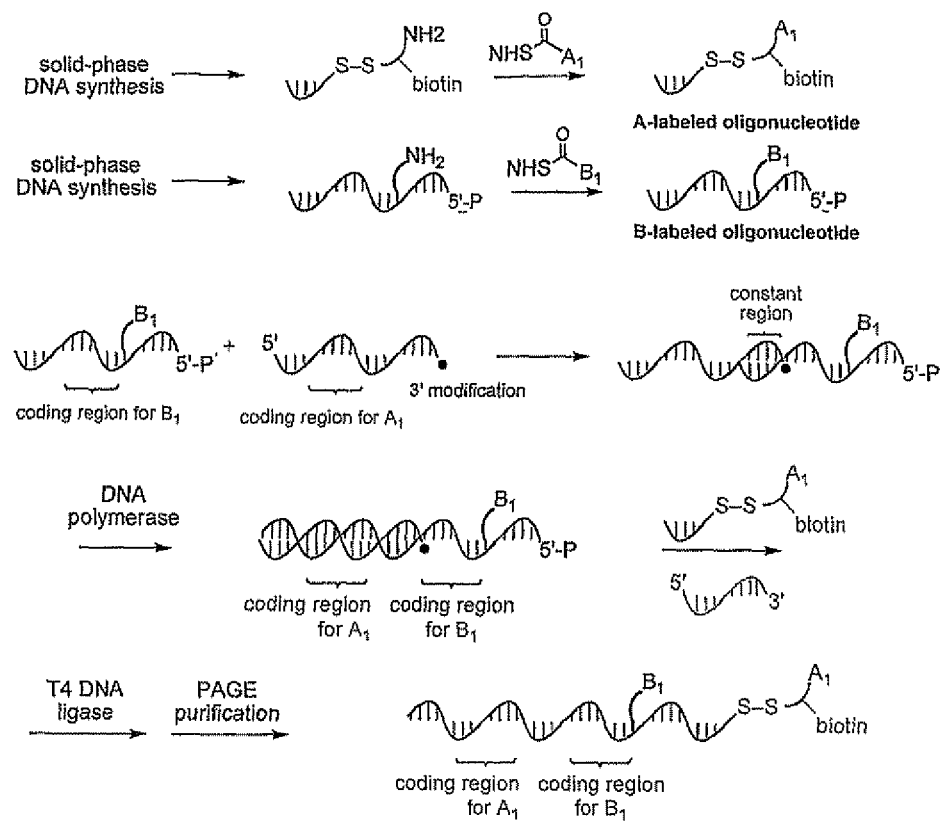
FIG. 4 illustrates an exemplary method of assembling the template molecules with attached substrates in the inventive reaction discovery system.

In certain embodiments, the method of preparing of the template is a modification of the method use to prepare templates in the two-pool reaction discovery system as described in U.S. application, U.S. Ser. No. 11/205,493, filed Aug. 17, 2005, incorporated herein by reference. This methods generally involves labeling an oligonucleotide with a single substrate and using enzymatic steps to assemble the full-length template. As shown in FIG. 4, the DNA with the internal substrate $B_1$ is prepared. This DNA is then annealed to another sequence encoding the $A_1$ substrate and by a primer extension reaction the encoding sequence for substrate $A_1$ is added to the sequence encoding the substrate $B_1$. The resulting DNA template contains the coding region for both substrates and is linked to one substrate of the pair. In the next step, a simple ligation appends an oligonucleotide with substrate $A_1$ attached to its 5' end via a cleavable affinity labeled linker to the 5' end of the template from the first step. The resulting full-length template contains the two coding regions for the two substrates. One substrate $A_1$ is attached to the 5' end through a cleavable linker with an affinity tag, and the other substrate $B_1$ is attached at an internal modified base. The full-length template with its combination of substrates may then be optionally purified using any technique known in the art including denaturing PAGE, HPLC, or column chromatography. In certain embodiments, the method is amenable to preparing a library of individual templates with substrates $A_1$-$A_n$ and substrates $B_1$-$B_n$. The template molecules are prepared individually or in parallel. In certain embodiments, the template molecules are prepared in parallel with 10-100 different template molecules being prepared at once. In certain embodiments, the template molecules are prepared in parallel with 10-30 different template molecules being prepared at once.

The resulting template molecules are also considered an aspect of the invention. In certain embodiments, the template molecule comprises an oligonucleotide with sequences to identify the attached substrates, two substrates, a cleavable linker attaching at least one of the substrates to the oligonucleotide, and an affinity agent for use in the selection process. In certain embodiments, the oligonucleotide also include primer sequences useful in preparing the template, useful in PCR amplification, and/or useful in sequencing or microarray analysis.

Kits

The invention also provides kits for practicing the inventive system. In certain embodiments, the kit includes all the materials needed by a researcher to conduct a round of reaction discovery. The kit may include all or some of the following: oligonucleotides, nucleotides, modified nucleotides, linkers, affinity reagents (e.g., biotin, antigens, epitopes, peptides, etc.), substrates, buffers, enzymes, materials for PAGE, columns, solvents, catalysts, reagents, ligands, microarrays, vials, Eppendorf tubes, instructions, etc. In certain embodiments, the kit may allow the user to provide his or her own substrates. In certain embodiments, the kit may allow the user to test his or her own reaction conditions. In certain embodiments, the materials in the kit are packaged conveniently for the researcher to use.

These and other aspects of the present invention will be further appreciated upon consideration of the following Examples, which are intended to illustrate certain particular embodiments of the invention but are not intended to limit its scope, as defined by the claims.

EXAMPLES

Example 1

Reaction Discovery in 100% Aqueous Solutions and Organic Solvent-Water Mixtures

Figure 5:
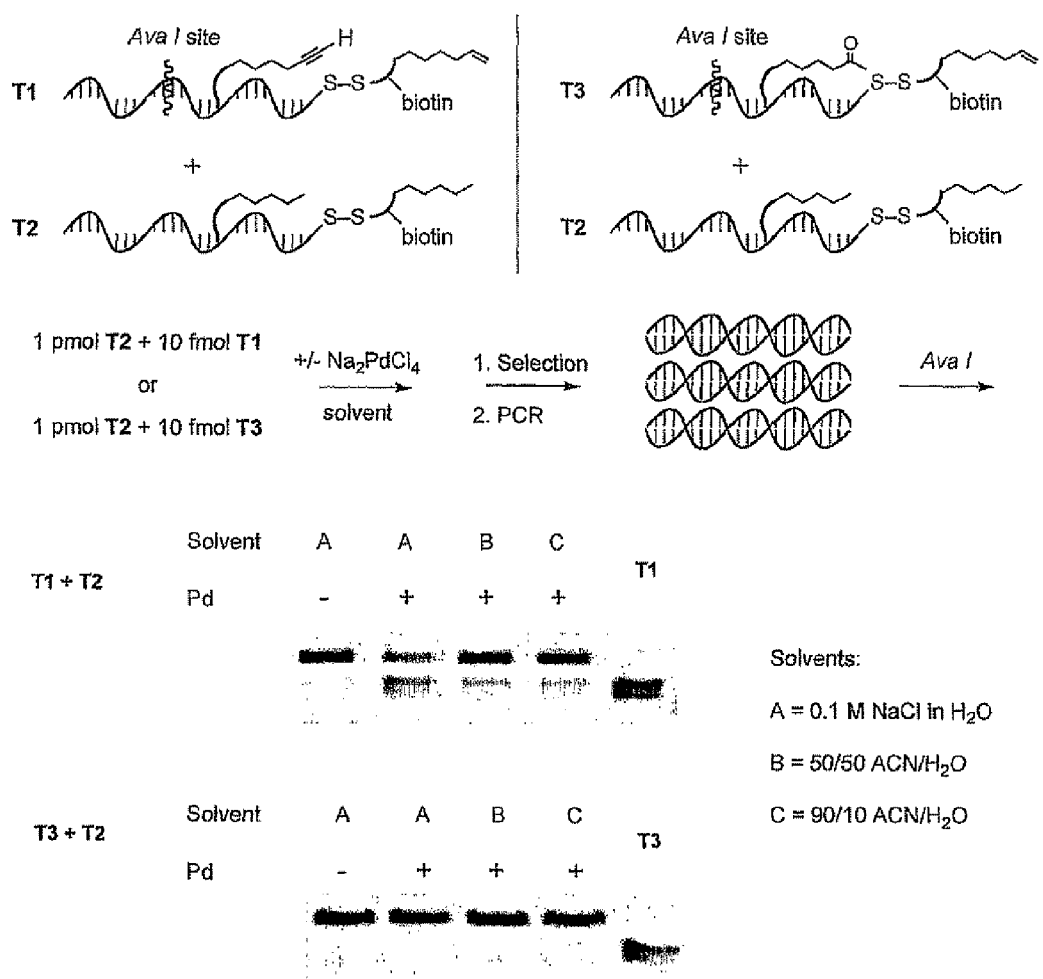
FIG. 5 shows the results of a model selection in the presence of $Na_2PdCl_4$.
Figure 6:
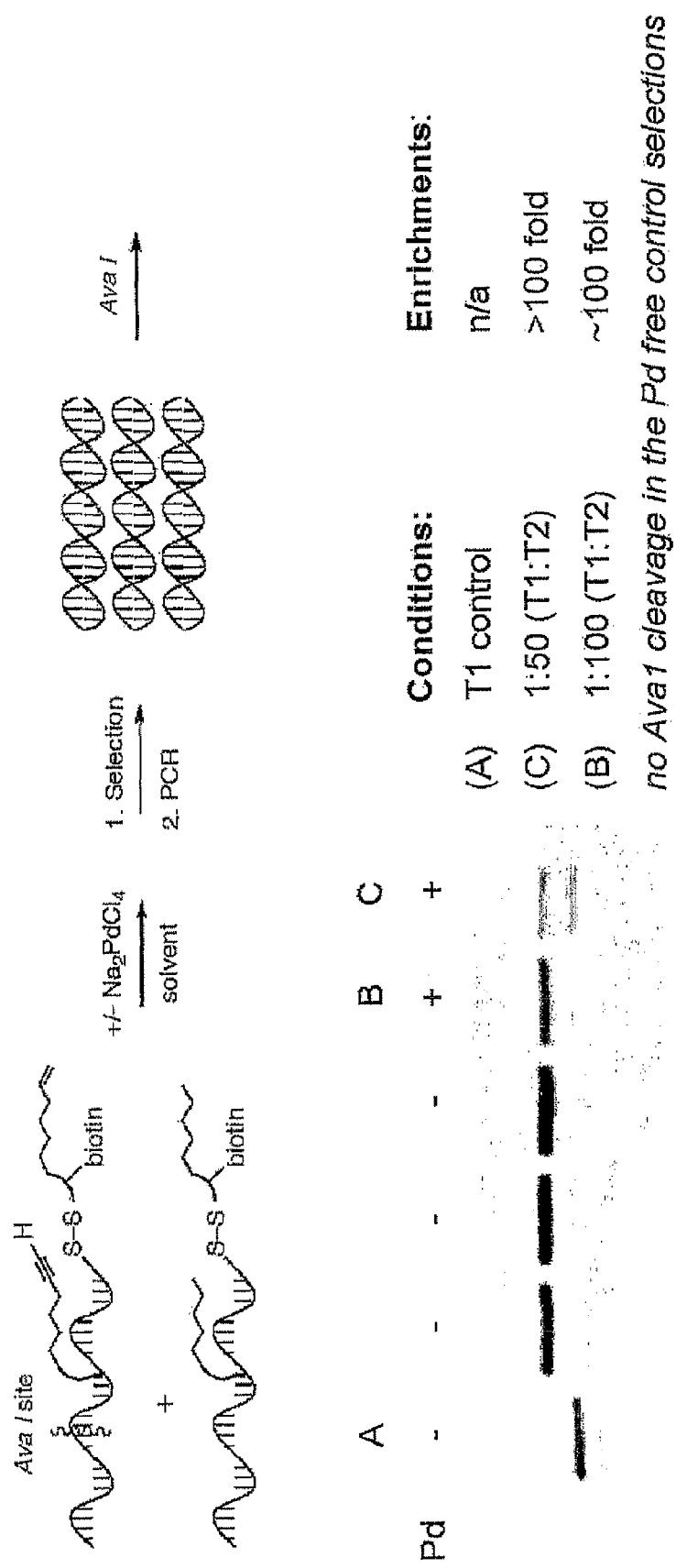
FIG. 6 shows the design of an experiment to test a new architecture with a shorter template, with a linker of 6 carbon atoms and a distance between the two substrates of 5 bases.

We tested the ability to select for reactions under conditions that do not favor duplex formation in a model experiment that included one sequence attached to a reactive combination of substrates and another sequence attached to a non-reactive combination (FIG. 5). The experiment was designed to mimic a reaction discovery selection wherein one substrate combination reacts to form a bond between the two substrates and the other combinations do not react. We separately prepared a template linked to a terminal alkene and a terminal alkyne (template T1) and a template linked to two alkanes (template T2) using the method described above. Fifteen bases separate the 5' end of the template to which one substrate is attached from the modified dT to which the other substrate is attached, a distance comparable to the separation between the 5' end of the template and the 3' end of the complementary DNA in the two-pool system. T1 contains a restriction site for the endonuclease Ava I that is not present in T2. T1 was combined with a 100-fold excess of T2 in an aqueous NaCl solution or a water-acetonitrile mixture. The solutions were treated with 500 μM $Na_2PdCl_4$, conditions under which an alkene and an alkyne react to form an enone, and selections for bond formation were performed as described above. The selected sequences were amplified by PCR and digested with Ava I to determine the enrichment of the sequence encoding the alkene and alkyne. Selection for bond formation in aqueous NaCl provided a ~130-fold enrichment of T1. Importantly, >50-fold enrichment of T1 was observed when selections were performed in either 50% ACN—$H_2O$ or in 90% ACN—$H_2O$ with 100 μM cetyl trimethylammonium bromide to enhance DNA solubility (Ijiro et al. A DNA-lipid complex soluble in organic solvents. *J. Chem. Soc. Chem. Comm.* 18, 1339-1341 (1992); Tanaka et al. A DNA-lipid complex in organic media and formation of an aligned cast film. *J. Am. Chem. Soc.* 118, 10679-10683 (1996); each of which is incorporated herein by reference). A control selection in which $Na_2PdCl_4$ was omitted showed no enrichment of T1.

Since the selection is designed only to separate biotin-linked sequences from non-biotin-linked sequences, it is possible that the enrichment observed for T1 upon exposure to $Na_2PdCl_4$ is a result of the alkene reacting with functionality on the DNA and not with the alkyne. To determine the extent to which this reactivity accounts for the enrichment of T1 in the experiment described above, we performed a selection where T1 was replaced with T3, a template with the same sequence as T1 but in which the alkyne was replaced with a ketone, a substrate that is not reactive with the alkene under the reaction conditions (Chapter 3). Under identical selection conditions, the enrichment of T3 was much less than that observed for T1 (FIG. 5). T3 was enriched <20 fold in 0.1 M NaCl and <10-fold in both 50% ACN/$H_2O$ and 90% ACN/$H_2O$. These results demonstrate that the enrichment observed for T1 is primarily a result of a bond-formation between the alkyne and the alkene and to a minor extent a result of the alkene reacting with functionality on the DNA. We speculate that Wacker-type addition of nucleophilic exocyclic amines on the DNA to a Pd-activated alkene accounts for low levels of bond-formation between DNA and the alkene.

The enrichment factors for T1 are modest considering the high affinity of the biotin-streptavidin interaction. Enrichment may be negatively affected by incomplete cleavage of the disulfide bonds, a low reactivity of the two substrates separated by 15 bases, or a Pd-specific increase in the background. Since a microarray-based analysis of a reaction discovery selection evaluates reactivity based on the relative abundance of individual sequences before and after selection (Chapter 3), we anticipate that the enrichment factors observed for the single-pool system in these model selections will yield readily detectable signals in an array analysis. Decreasing the separation between the two substrates may also increase the signal arising from reactive substrate combinations.

Experimental Methods

General Methods.

DNA synthesis was carried out using standard reagents and protocols as described in Chapter 2 with exceptions noted below. Oligonucleotides were cleaved off of the CPG resin using AMA treatment for 10 min at 65° C., purified by reversed-phase HPLC and quantitated by UV spectroscopy. The A-labeled and B-labeled oligonucleotides were prepared using the indicated carboxylic acids and the labeling procedures described in Chapter 3. Labeled oligonucleotides were characterized by MALDI-TOF MS and observed masses were within 0.075% of calculated masses. The preparations of the A-coding oligonucleotide and splint oligonucleotides used in the template assemblies were described in Chapter 3.

Preparation of A-Labeled Oligonucleotides.

DNA synthesis was carried out using standard reagents and monomers and three modified phosphoramidites: 5' Amino-Modifier-5, Biotin phosphoramidite, and Thiol-Modifier C6 S-S (all from Glen Research). The standard protocol was modified to include double deblocking and triple capping for the cycle incorporating the thiol-modifier phosphoramidite. This modification was made to minimize the possibility of truncation byproducts that lack the disulfide linkage and are therefore permanently linked to biotin. The oligonucleotide was labeled with hexanoic acid (Aldrich) (calculated mass: 4044.90; observed mass: 4045±3) and 6-hexenoic acid (Aldrich) (calculated mass: 4056.90; observed mass: 4057±3).

Preparation of B-Labeled Oligonucleotides.

DNA synthesis was carried out using standard reagents and monomers and two modified phosphoramidites: Chemical Phosphorylating Reagent II and Amino-Modifier C6 dT (both from Glen Research). The sequence B1 contains a restriction site for Ava I and the sequence B2 lacks this site. The 5' phosphate group on each oligonucleotide was exposed with 2:1 $H_2O$:concentrated $NH_4OH$ using the manufacturer's protocol (Glen Research) either before or after labeling. B1 was labeled with 6-heptynoic acid (Aldrich) (calculated mass: 9105.63; observed mass: 9107±7) and 6-oxoheptanoic acid (Aldrich) (calculated mass: 9123.64; observed mass: 9123±7). B2 was labeled with hexanoic acid (calculated mass: 9135.65; observed mass: 9134±7).

Assembly of DNA Templates Linked to Two Substrates.

The full-length templates linked to two substrates were assembled in a two step sequence consisting of primer extension and ligation analogous to the modular assembly of pool A templates (FIG. 4). Primer extension was typically performed on a 300 pmol scale (5 μM A-coding oligonucleotide and 5 μM B-labeled oligonucleotide) in 60 μL at 25° C. for 1 h using Klenow exo⁻ (New England BioLabs). Ligations were performed directly following buffer exchange of the primer extension reactions. Three-hundred pmol of A-labeled oligonucleotide and 300 pmol of the appropriate splint oligonucleotide were added to the buffer-exchanged reaction and the ligations were performed at 16° C. for 2 h. Ligation reactions were ethanol precipitated and purified by denaturing PAGE according to standard procedures. Typically, a 300 pmol preparation yielded 100 pmol of purified full-length template. The following templates were assembled with this procedure and used in the model selections: A-labeled 6-heptenoic acid+B1-labeled 6-heptynoic acid (T1), A-labeled hexanoic acid+B2-labeled hexanoic acid (T2), and A-labeled 6-heptenoic acid+B1-labeled 6-oxoheptanoic acid (T3).

Selections with Na$_2$PdCl$_4$.

One pmol of T2 and 10 fmol of either T1 or T3 were combined in the solvents indicated in FIG. 5 and exposed to 500 μM Na$_2$PdCl$_4$. The total volume in each case was 30 μL. After 20 min at 25° C., 10 μL of 0.1 M dithiothreitol (Aldrich) was added to the solution, followed by 150 μL of 0.1 M TCEP in 1.0 M phosphate pH 8.0. Disulfide cleavage was allowed to proceed for 1 h at 25° C. The solution was diluted with 150 μL H$_2$O and an aliquot of streptavidin magnetic particles (Roche Biosciences) with a 22 pmol binding capacity was added directly. Binding to streptavidin was allowed to proceed for 10 min and then the supernatant was removed and the particles were washed twice with 200 μL of 1.0 M NaCl, 10 mM Tris, 1 mM EDTA pH 7.5 ("wash buffer"). The particles were resuspended in 20 μL of 95% formamide-5% 10 mM EDTA pH 8.0 ("elution solution") and heated at 65° C. for 10 min. Fifteen μL of this eluant was added directly to 100 μL of fresh 0.1 M TCEP in 1.0 M phosphate pH 8.0. After 40 min at 25° C., the solution was diluted with 100 μL H$_2$O and a fresh aliquot of streptavidin particles was added directly. The supernatant was removed after 10 min and the particles were washed twice with 200 μL wash buffer. The particles were resuspended in 20 μL of elution solution and heated at 90° C. for 10 min. Fifteen μL of this eluant was added to 45 μL of H$_2$O and the resulting solution was passed through a gel filtration spin column (Princeton Separations) to remove formamide. The eluant was used directly in PCR reactions.

PCR and Ava I Digest Analysis of Selections.

For each selection, a 2.5 μL aliquot of the final eluant (Selections with Na$_2$PdCl$_4$) was added to a 50 μL PCR reaction containing 2.5 mM MgCl$_2$, 0.2 M dNTPs, and 500 nM of each primer. The sequences were amplified with 25 cycles of 95° C. for 30 s, 55° C. for 30 s, and 72° C. for 20s. Five μL aliquots of the PCR reactions were run on a 3% agarose gel to determine relative amounts of PCR products and the remaining 45 μL of each PCR reaction was precipitated with ethanol. Typically, one-fourth of the precipitated material (approximately 5 pmol of PCR product) was digested with 10 U of Ava I (New England Biolabs) for 2 h at 37° C. The digests were run on a 3% agarose gel and quantitated by CCD-based densitometry.

DNA Sequences and Linker Structures.

Full-length template sequence (SEQ ID NOs: 1-2):

5'-CGTTGATATCCGCAGTXXXXXXXXXXXXXXXCACACACCACGTATAG CG GTGCCAGCTGCTAGCTT-3' where XXXXXXXXXXXXXXX is either AACTTCCTCTCGGGA (SEQ ID NO: 1) or ACGCGATGTTTCGAC (SEQ ID NO: 2) and T represents the amino-modified dT to which a substrate is attached.

Structure of the 5' end of a full-length template:

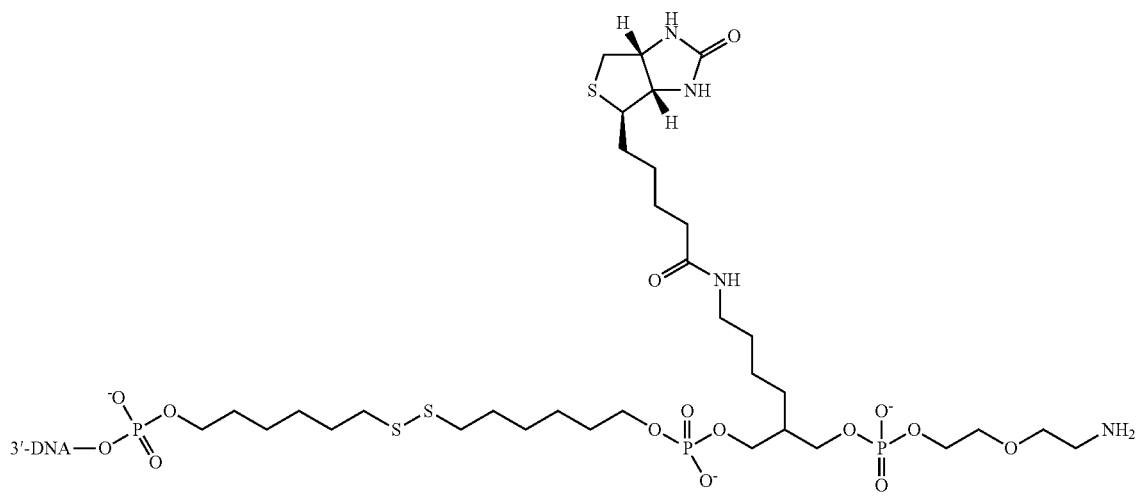

Structure of T:

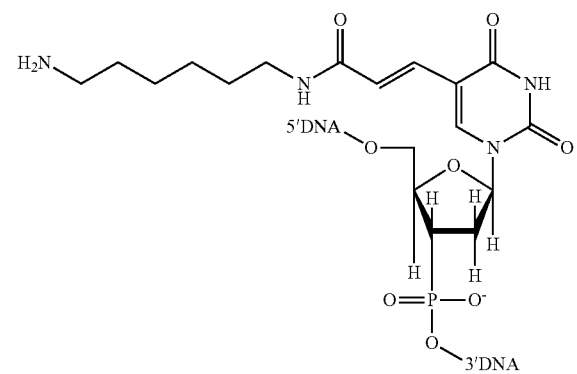

Example 2

General Reaction Discovery Experimental

Figure 21:
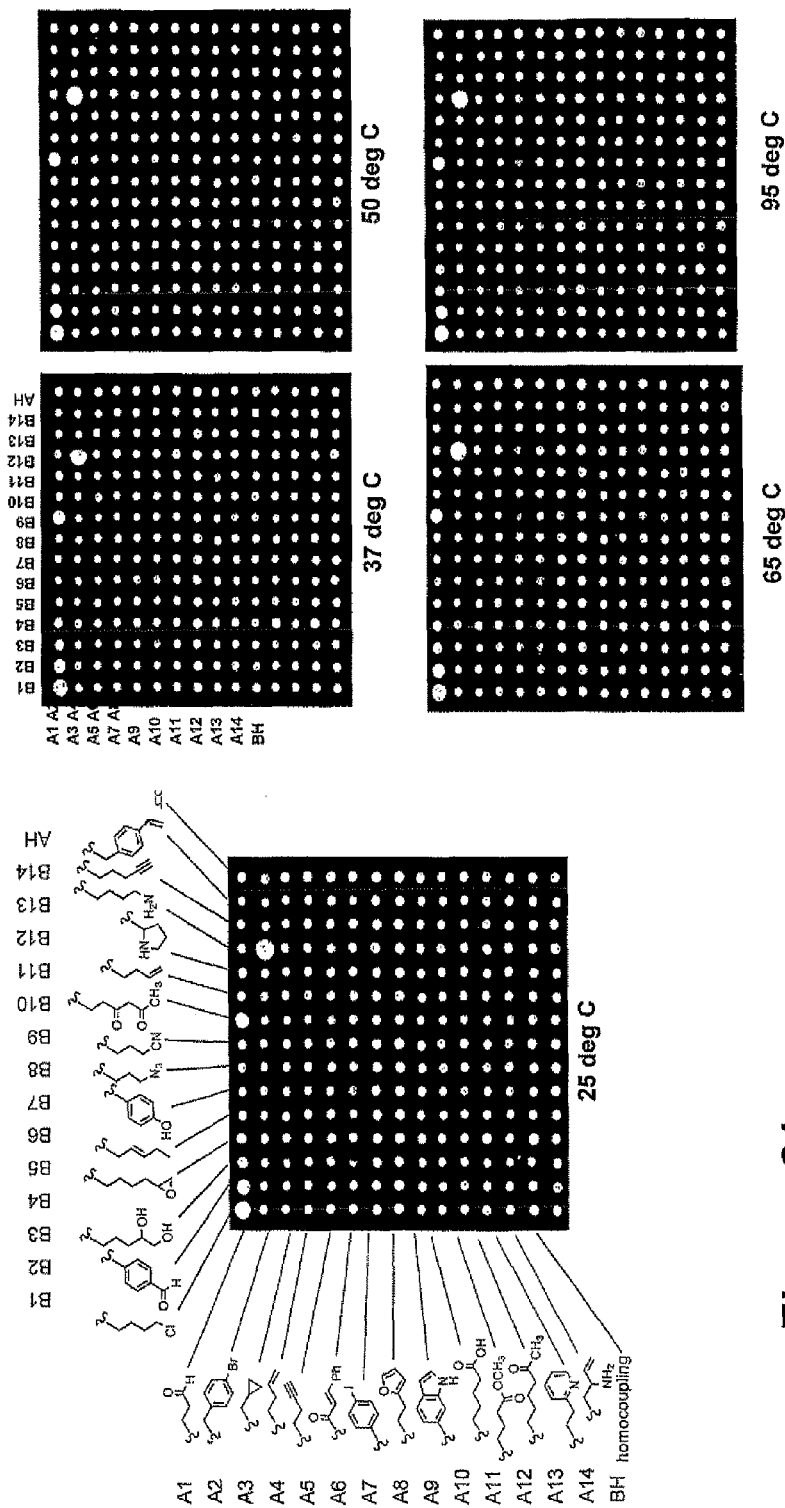
FIG. 21 demonstrates the use of the reaction discovery system to screen for bond forming reaction mediated by Pd(II). Reaction conditions included 1 mM Pd(II) in 90% acetonitrile for 20 minutes at four different temperatures: 37° C., 50° C., 65° C., and 95° C.
Figure 22:
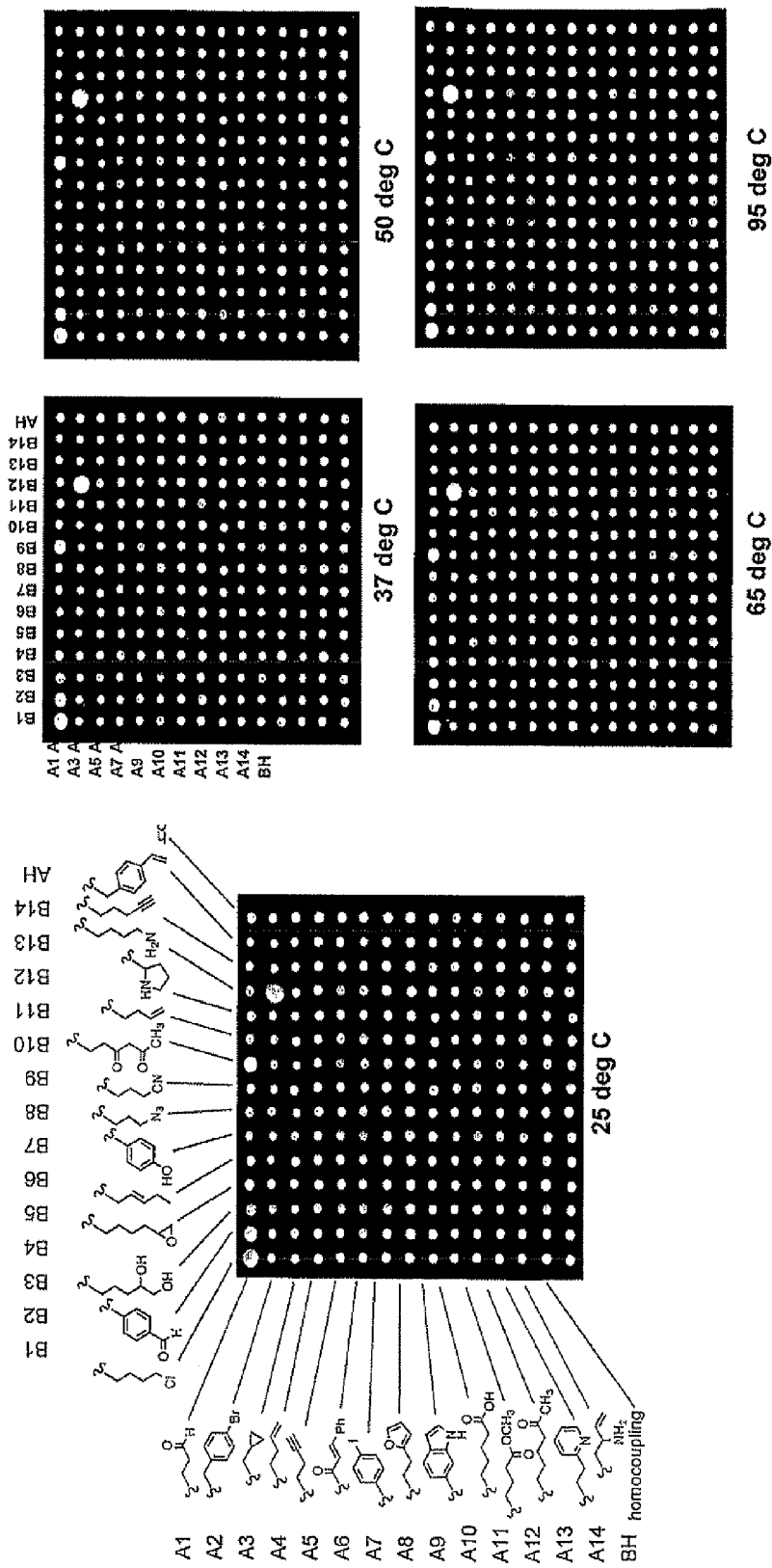
FIG. 22 demonstrates the use of the reaction discovery system to screen for bond forming reaction mediated by Pd(II). Reaction conditions included 1 mM Pd(II) in 90% DMSO for 20 minutes at four different temperatures: 37° C., 50° C., 65° C., and 95° C.

The single pool reaction discovery starting material pool was assembled by combining 224 unique DNA template molecules at equal concentration and an internal standard at one tenth that concentration. This reaction discovery pool was prepared at a concentration of 0.5 μM and stored at −20° C. In a typical reaction discovery experiment, 1 pmol of total material (i.e., 2 μL of the staring reaction discovery pool) was combined with combined at the designated concentrations and solvents as noted in a 100 μL, 200 μL, or 300 μL total volume. For example, in the case of the palladium (II) chemistry, 2 μL of starting pool was combined with 10 μL of Pd(II) (20 mM $Na_2PdCl_4$ in double distilled water), 8 μL of doubly distilled water, and 180 μL of organic solvent (either acetonitrile or DMSO). Results for Pd(II) chemistry experiments are shown in FIGS. 20-22. In the case of the aqueous reaction reactions, the volume was adjusted with 100 mM MOPS buffer (pH 7) with 1 M NaCl in double distilled water. The reactions were then incubated at the designated temperature for the designated amount of time. After the reactions were complete, the DNA template molecules were precipitated with ethanol, and selections for bond formation were carried out. See FIGS. 17-22.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of identifying new chemical reactions, the method comprising steps of:
   providing one or more single-stranded DNA templates,
   wherein each template has a unique pair of substrates covalently linked to the template;
   wherein each substrate comprises one or more functional groups selected from the group consisting of aliphatic halides, aryl halides, esters, amides, carbonates, carbamates, ureas, alcohols, thiols, amines, alkyls, alkenes, alkynes, aryls, heteroaryls and phosphorus-containing groups;
   wherein a portion of the sequence of the single-stranded DNA template encodes the identity of the two substrates covalently linked to the template; and
   wherein one of the two substrates and biotin is covalently linked to the template through a cleavable linker;
   subjecting the single-stranded DNA templates with the substrates covalently linked to the template to reaction conditions,
   whereby a covalent bond is formed directly between each of the two different substrates covalently linked to a single template;
   cleaving the cleavable linker;
   selecting unique substrate pairs that reacted to form the a covalent bond between the two substrates that form the unique pair of substrates covalently linked to the template using streptavidin; and
   identifying the selected unique substrate pairs that reacted using the encoded single-stranded DNA template covalently liked to the unique substrate pairs and reaction conditions.

2. The method of claim 1, wherein the step of identifying comprises: amplifying the single-stranded DNA template covalently liked to the selected unique substrate pairs that reacted using PCR; and sequencing the amplified DNA.

3. The method of claim 1, wherein the step of identifying comprises using a microarray to identify the single-stranded DNA template covalently liked to the selected unique substrate pairs that reacted.

* * * * *

UNITED STATES PATENT AND TRADEMARK OFFICE
CERTIFICATE OF CORRECTION

PATENT NO. : 8,691,729 B2  
APPLICATION NO. : 11/971642  
DATED : April 8, 2014  
INVENTOR(S) : David R. Liu et al.

Page 1 of 1

It is certified that error appears in the above-identified patent and that said Letters Patent is hereby corrected as shown below:

*In the Specification*

At column 1, lines 3-8, please amend the "Related Applications" section as shown below:

RELATED APPLICATIONS

The present application <u>is a continuation of and claims priority under 35 U.S.C. §120 to international PCT application number PCT/2006/027354, filed July 14, 2006, which</u> claims priority under 35 U.S.C. §119(e) to U.S. provisional patent application, U.S. Ser. No. 60/699,735, filed Jul. 15, 2005, <u>each of which is</u> incorporated herein by reference.

*In the Claims*

In claim 1, column 26, lines 27-28, please change the language "selecting unique substrate pairs that reacted to form the a covalent bond" to --selecting unique substrate pairs that reacted to form a covalent bond--.

In claim 1, column 26, lines 32-33, please change the language "covalently liked to the unique substrate pairs and reaction conditions" to --covalently linked to the unique substrate pairs and reaction conditions--.

In claim 2, column 26, lines 36-37, please change the language "covalently liked to the selected unique substrate pairs that reacted using PCR" to --covalently linked to the selected unique substrate pairs that reacted using PCR--.

In claim 3, column 26, lines 40-41, please change the language "DNA template covalently liked to the selected unique substrate pairs that reacted" to --DNA template covalently linked to the selected unique substrate pairs that reacted--.

Signed and Sealed this  
Twenty-third Day of September, 2014

Michelle K. Lee  
*Deputy Director of the United States Patent and Trademark Office*

SEQUENCE LISTING

```
<160> NUMBER OF SEQ ID NOS: 19

<210> SEQ ID NO 1
<211> LENGTH: 66
<212> TYPE: DNA
<213> ORGANISM: ARTIFICIAL SEQUENCE
<220> FEATURE:
<223> OTHER INFORMATION: synthetic polynucleotide

<400> SEQUENCE: 1
cgttgatatc cgcagtaact tcctctcggg acacacacca cgtatagcgg tgccagctgc      60
tagctt                                                                66

<210> SEQ ID NO 2
<211> LENGTH: 66
<212> TYPE: DNA
<213> ORGANISM: ARTIFICIAL SEQUENCE
<220> FEATURE:
<223> OTHER INFORMATION: synthetic polynucleotide

<400> SEQUENCE: 2
cgttgatatc cgcagtacgc gatgtttcga ccacacacca cgtatagcgg tgccagctgc      60
tagctt                                                                66

<210> SEQ ID NO 3
<211> LENGTH: 18
<212> TYPE: DNA
<213> ORGANISM: ARTIFICIAL SEQUENCE
<220> FEATURE:
<223> OTHER INFORMATION: synthetic polynucleotide
<220> FEATURE:
<221> NAME/KEY: misc_feature
<222> LOCATION: (10)..(10)
<223> OTHER INFORMATION: n is a, c, g, or t

<400> SEQUENCE: 3
atccgcagan cacacacc                                                   18

<210> SEQ ID NO 4
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 4
atccgcagaa cttcctctcg ggacacacac c                                    31
```

```
<210> SEQ ID NO 5
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 5
atccgcagac gcgatgtttc gaccacacac c                              31

<210> SEQ ID NO 6
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 6
atccgcagag cgttatggtc cgacacacac c                              31

<210> SEQ ID NO 7
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 7
atccgcagac atgagcccca ctacacacac c                              31

<210> SEQ ID NO 8
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 8
atccgcagcc actgttacta gggcacacac c                              31

<210> SEQ ID NO 9
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 9
atccgcagcg tgcttgagga gaacacacac c                              31

<210> SEQ ID NO 10
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 10
atccgcagag gcctctttag acccacacac c                              31

<210> SEQ ID NO 11
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 11
```

```
atccgcagct tagtttcgcg caccacacac c                              31
```

<210> SEQ ID NO 12
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 12

```
atccgcagga gggtgatgca tgtcacacac c                              31
```

<210> SEQ ID NO 13
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 13

```
atccgcaggc tggactagct acacacacac c                              31
```

<210> SEQ ID NO 14
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 14

```
atccgcagta gacacgcatg tgccacacac c                              31
```

<210> SEQ ID NO 15
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 15

```
atccgcagtc ggactttgat ggccacacac c                              31
```

<210> SEQ ID NO 16
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 16

```
atccgcagac cgaagggcaa taccacacac c                              31
```

<210> SEQ ID NO 17
<211> LENGTH: 31
<212> TYPE: DNA
<213> ORGANISM: ARTIFICIAL SEQUENCE
<220> FEATURE:
<223> OTHER INFORMATION: synthetic polynucleotide

<400> SEQUENCE: 17

```
atccgcaggt aagcccttgg tatcacacac c                              31
```

<210> SEQ ID NO 18
<211> LENGTH: 18
<212> TYPE: DNA
<213> ORGANISM: ARTIFICIAL SEQUENCE

```
<220> FEATURE:
<223> OTHER INFORMATION: synthetic polynucleotide
<220> FEATURE:
<221> NAME/KEY: misc_feature
<222> LOCATION: (10)..(10)
<223> OTHER INFORMATION: n is a, c, g, or t

<400> SEQUENCE: 18
atccgcagan cacacacc                                                       18

<210> SEQ ID NO 19
<211> LENGTH: 31
<212> TYPE: DNA
<213> ORGANISM: ARTIFICIAL SEQUENCE
<220> FEATURE:
<223> OTHER INFORMATION: syntehtic polynucleotide

<400> SEQUENCE: 19
atccgcagtt gatgaccagg ccacacacac c                                         31
```